US008557554B2

(12) United States Patent
Connolly et al.

(10) Patent No.: US 8,557,554 B2
(45) Date of Patent: Oct. 15, 2013

(54) MUTATION OF DNA POLYMERASES FROM ARCHAEOBACTERIA

(75) Inventors: Bernard Connolly, Newcastle upon Tyne (GB); Mark Fogg, York (GB); Laurence H Pearl, London (GB)

(73) Assignee: The University of Newcastle (GB)

( * ) Notice: Subject to any disclaimer, the term of this patent is extended or adjusted under 35 U.S.C. 154(b) by 1732 days.

(21) Appl. No.: 10/511,130

(22) PCT Filed: Apr. 15, 2003

(86) PCT No.: PCT/GB03/01623
§ 371 (c)(1),
(2), (4) Date: Aug. 15, 2005

(87) PCT Pub. No.: WO03/089637
PCT Pub. Date: Oct. 30, 2003

(65) Prior Publication Data
US 2006/0057682 A1   Mar. 16, 2006

(30) Foreign Application Priority Data
Apr. 17, 2002 (GB) .................................. 0208768.2

(51) Int. Cl.
*C12N 9/12* (2006.01)
(52) U.S. Cl.
USPC ............................ 435/194; 435/183; 530/350
(58) Field of Classification Search
None
See application file for complete search history.

(56) References Cited

U.S. PATENT DOCUMENTS 5,827,716 A * 10/1998 Mamone ....................... 435/194

FOREIGN PATENT DOCUMENTS

| EP | 1 088 891 A1 | 4/2001 |
| WO | WO 01/38546 A1 | 5/2001 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Fogg et al., Structural basis for uracil recognition by archaeal family B DNA polymerases, Nature Structural Biology (UK), vol. 9 ( No. 12), pp. 922-927, (Dec. 2002).
Greagg et al., A read-ahead function in archaeal DNA polymerases detects promutagenic template-strand uracil, Proc. Natl. Acad. Sci. USA, pp. 9045-9050, (Aug. 1999).
Evans et al., Improving dideoxynucleotide-triphosphate utilisation by the hyper-thermophilic DNA polymerase from the archaeon *Pyrococcus furiosus*, Nucleic Acids Research, Oxford University Press, vol. 28 ( No. 5), pp. 1059-1066, (2000).
Connolly et al., Uracil recognition by archaeal family B DNA polymerases, Biochemical Society, vol. 31 ( No. 3), pp. 699-702, (2003).
Patel et al., Multiple Amino Acid Substitutions Allow DNA Polymerases to Synthesize RNA, The Journal of Biological Chemistry, The American Society for Biochemistry and Molecular Biology, Inc., vol. 275 ( No. 51), pp. 40266-40272, (2000).
Lasken et al., Archaebacterial DNA Polymerases Tightly Bind Uracil-containing DNA, The Journal of Biological Chemistry, The American Society for Biochemistry and Molecular Biology, Inc., vol. 271 (No. 30), pp. 17692-17696, (1996).
Hopfner et al., Crystal structure of a thermostable type B DNA polymerase from *Therococcus gorgonarius*, Proc. Natl. Acad. Sci. USA, vol. 96, pp. 3600-3605, (Mar. 1999).
N. Guex and M. C. Peitsch., Swiss-Model and the Swiss-PdbViewer: An environment for comparative protein modeling, Electrophoresis, vol. 18 (No. 15), pp. 2714-2723, (1997).
Rodriguez et al., Crystal Structure of a Pol α Family DNA Polymerase from the Hyperthermophilic Archaeon *Thermococcus* sp. 9•N-7, J. Mol. Biol., vol. 299 (No. 2), pp. 447-462, (2000).
T. Yamane, NMR Studies of nucleic acids, Procedures in Nucleic Acid Research, vol. 2, pp. 262-310, (1966).
Wang et al., Crystal Structure of a pol α Family Replication DNA polymerase from Bacteriophage RB69, Cell, vol. 89 (No. 7), pp. 1087-1099, (Jun. 1997).
Franklin et al., Structure of the Replicating Complex of a Pol α Family DNA Polymerase, Cell, vol. 105 (No. 5), pp. 657-667, (Jun. 2001).
Zhao et al., Crystal structure of an archaebacterial DNA polymerase, Structure, vol. 7 (No. 10), pp. 1189-1199, (1999).
Hashimoto et al., Crystal Structure of DNA Polymerase from Hyperthermophilic Archaeon *Pyrococcus kodakaraensis* KOD1, J. Mol. Biol., vol. 306, pp. 469-477, (2001).
Thompson et al., The CLUSTAL_X windows interface: flexible strategies for multiple sequence alignment aided by quality analysis tools, Nucleic Acids Research, vol. 25 (No. 24), pp. 4876-4882, (1997).
R. Sayle and J. F. Milner-White, RASMOL: biomoleular graphics for all, Trends Biochem. Sci., vol. 20 (No. 9), pp. 374-376, (Sep. 1995).
Hogrefe et al., Archaeal dUTPase enhances PCR amplifications with archaeal DNA polymerases by preventing dUTP incorporation, Proc. Natl. Acad. Sci. USA, vol. 99 (No. 2), pp. 596-601, (Jan. 2002).
Wang et al., Crystal Structures of an NH2-Terminal Fragment of T4 DNA Polymerase and Its Complexes with Single-Stranded DNA and with Divalent Metal Ions, Biochemistry, vol. 35 (No. 25), pp. 8110-8119, (1996).
Reid et al., Binding and Recognition of GATATC Target Sequences by the EcoRV Restriction Endonuclease: A Study Using Fluorescent Oligonucleotides and Fluorescence Polarization, Biochemistry, vol. 40 (No. 8), pp. 2484-2494, (2001).

* cited by examiner

*Primary Examiner* — Richard Hutson
(74) *Attorney, Agent, or Firm* — Pillsbury Winthrop Shaw Pittman LLP

(57) ABSTRACT

The present invention relates to a variant archaeal DNA polymerase having a modified amino acid sequence of a wild-type amino acid sequence, the modified sequence being in the amino-terminal amino acids that comprise a uracil-binding pocket in the wild-type polymerase whereby the variant polymerase has reduced affinity for uracil than the wild-type polymerase. Such variant polymerases may be usefully employed in biological assay systems such as the polymerase chain reaction.

6 Claims, 7 Drawing Sheets

FIG. 1

Figure 2:
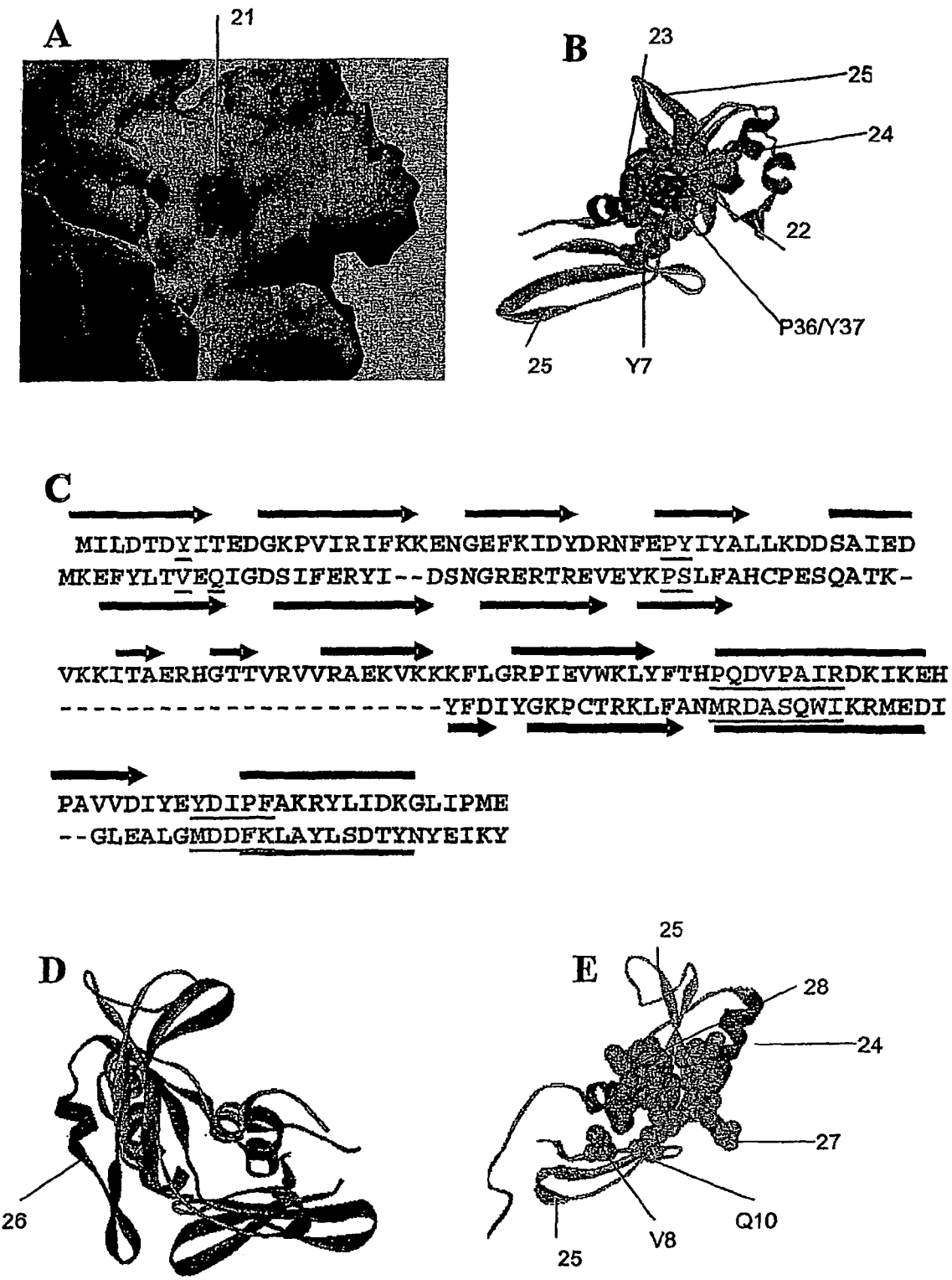

| | | | | | |
|---|---|---|---|---|---|
| Pfu | 41 | :----------------------------------LLRDDSKIEEVKKITGERHGKITYDVEKKEIG | : | 77 |
| Tgo | 41 | :----------------------------------LLKDDSAIEDVKKITRERHGTVVKVEKKEIG | : | 77 |
| PKOD | 41 | :----------------------------------LLKDDSAIEEVKKITRERHGTVVKVEKKVQG | : | 77 |
| BTok | 41 | :----------------------------------LLKDDSAIEDIKKITRERNGTVVRVTRAEVEKKEIG | : | 77 |
| 9°N-7 | 41 | :----------------------------------LLKDDSAIEDVKKITRERHGTVVKVEKRAEVQKKEIG | : | 77 |
| Tli | 41 | :----------------------------------LLKDDSRIEEIKLGERHGKTVRVLDAVIVERKEIG | : | 77 |
| Mvo | 46 | :KEIYDYLDGLNQEIDLKKLEPEFNNTSLKVQDLITNIEIEKIVYSDYIUNGKDISEVS | : | 105 |
| Pis | 46 | :----------------------------------VDCRVCEPARLKTALS-RVAPIDDVQIVERREIG | : | 78 |
| Rfu | 47 | :----------------------------------IGVDEDILKNRTSTRR---EVIKLKSFERQLKTIG | : | 80 |
| Csy | 54 | :----------------------------------R-QPPSELGEL---BGREDVLGTEQVMEHDLLADK | : | 84 |
| Sac | 92 | :----------------------------------D-IDPDKUNKI-TKVVRDPSEDHLELINVDPYTGK | : | 125 |
| Soh | 93 | :----------------------------------D-IDPEKUNKI-PKVVRDPSEDHLETVHNDPYSGN | : | 126 |
| Sso | 93 | :----------------------------------D-LEPDKVGKI-PKIVRDPSEDHIETVSIDPYTWN | : | 126 |
| Poc | 129 | :----------------------------------D-IPPDKLQEL-HEVVDHKEDHVEVVIEVEDLLEWQ | : | 162 |
| Rpe | 173 | :----------------------------------D-ARPEDLRARGTDVSMDESFLQYDLVEVENPIDRK | : | 207 |

FIG.1 continued

FIG. 1 continued

MUTATION OF DNA POLYMERASES FROM ARCHAEOBACTERIA

This application is the National Phase of International Application PCT/GB03/01623, filed 15 Apr. 2003 which designated the U.S. and that International Application was published under PCT Article 21(2) in English.

The present invention relates to archaeal DNA polymerase variants and their use in the amplification of DNA.

Polymerase chain reaction (PCR) is a method whereby a sequence of DNA may be selectively amplified to produce a large sample that may be readily analyzed. A solution containing the DNA to be amplified, together with free bases, a polymerase enzyme and primers that bind to opposite ends of the two strands of the DNA segment to be replicated, is heated to break the bonds between the strands of DNA. When the solution cools, the primers bind to the separated strands and the polymerase builds a new strand by joining free bases to the primers thereby producing a new strand that is restricted solely to the desired segment. PCR enables billions of copies of a small piece of DNA to be produced in several hours.

Heat stable polymerases are required for this process and one of the most commonly used is Taq DNA polymerase from *Thermus aquaticus*. However, this enzyme does not possess a 3'-5' exonuclease III function, commonly referred to as "proofreading activity". This function removes bases that are mismatched at the 3' end of a primer-template duplex. The inability of Taq DNA polymerase to carry out this function results in it being prone to base incorporation errors.

Archaeal DNA polymerases are thermally stable and demonstrate proofreading activity. However, native archaeal DNA polymerases are inhibited by deoxyuracil. Archaeal DNA polymerases have a "read-ahead" function specifically for uracil. This template checking activity scans the template ahead of the replication fork for the presence of uracil and stalls polymerisation when uracil is encountered. Thus, the presence of deoxyuracil in DNA causes amplification to be stalled when using native archaeal DNA polymerases. This is a serious setback since the repetitive heating and cooling cycles of a DNA sample being amplified by PCR results in partial, thermally induced deamination of dCTP (a component incorporated into newly amplified DNA) to dUTP (which can be incorporated into DNA) and deamination of deoxycytidine in the DNA to deoxyuracil. This can result in the native archaeal DNA polymerases being unsuitable for PCRs, in particular those concerned with the prevention of "carry-over contamination" where PCR is carried out with dUTP rather than dTTP.

It is an object of the present invention to provide modified archaeal DNA polymerases that do not have the disadvantage of being inhibited by deoxyuracil and are particularly useful in polymerase chain reactions.

Accordingly, a first aspect of the present invention provides a variant archaeal DNA polymerase having a modified amino acid sequence of a wild-type amino acid sequence, the modified sequence being in the amino-terminal amino acids that comprise a uracil-binding pocket in the wild-type polymerase whereby the variant polymerase has reduced affinity for uracil compared to wild-type archaeal DNA polymerases.

The present invention is based upon research (see the Examples) conducted by the inventors that has identified a uracil-binding pocket in archaeal DNA polymerases. They realised that this pocket may be altered to provide variant polymerases according to the invention that may be beneficially used as described herein.

The variant archaeal DNA polymerase may be a modification of an archaeal family B DNA polymerase. For instance the variant may be derived from any one of the fourteen archaeal family B DNA polymerase shown in FIG. 1. For instance the variant may be derived from the polymerases found in *Pyrococcus furiosus* (Pfu-Pol), *Thermococcus gorgonarius* (Tgo-Pol), *Thermococcus litoralis* (Tli-Pol), *Thermococcus* sp. 9°N-7 (9°N-7-Pol), *Desulfurococcus* strain Tok (DTok-Pol), *Pyrobaculum islandicum* (Pis-Pol), *Archaeoglobus fulgidus* (Afu-Pol), *Sulfolobus acidocaldarius* (Sac-Pol), *Sulfurisphaera ohwakuensis* (Soh-Pol), *Sulfolobus solfataricus* (Sso-Pol), *Pyrodictium occultum* (Poc-Pol) or *Aeropyrum pernix* (Ape-Pol). It will be appreciated that the variant could also be derived from any other archaeal family B DNA polymerase.

It is preferred that the variant is derived from *Pyrococcus furiosus* (Pfu-Pol). Pfu-Pol used by the inventors has the following amino acid sequence:

```
MAILDVDYITEEEGKPVIRLFKKENGKFKIEHDRTFRPYIYALLRDDSKIEEVKKITGERHGKIVRIVDVEK  (SEQ ID NO. 1)

VEKKFLGKPITVWKLYLEHPQDVPTIREKVREHPAVVDIFEYDIPFAKRYLIDKGLIPMEGEEELKILAF

DIETLYHEGEEFGKGPIIMISYADENEAKVITWKNIDLPYVEVVSSEREMIKRFLRIIREKDPDIIVTYN

GDSFDFPYLAKPAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLVGQPLWDVSRSSTG

NLVEWFLLRKAYERNEVAPNKPSEEEYQRRLRESYTGGFVKEPEKGLWENIVYLDFFALYPSIIITHNVS

PDTLNLEGCKNYDIAPQVGHKFCKDIPGFIPSLLGHLLEERQKIKTKMKETQDPIEKILLDYRQKAIKLL

ANSFYGYYGYAKARWYCKECAESVTAWGRKYIELVWKELEEKFGFKVLYIDTDGLYATIPGGESEEIKKK

ALEFVKYINSKLPGLLELEYEGFYKRGFFVTKKRYAVIDEEGKVITRGLEIVRRDWSEIAKETQARVLET

ILKEGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS
```

The Pfu Pol used by the inventors contains an extra A at position 2. This extra amino acid was incorporated because it improves protein expression without affecting the properties of the enzyme. The true wild type Pfu Pol begins MILDVDY. The sequence of the true wild type is:

```
MILDVDYITEEGKPVIRLFKKENGKFKIEHDRTFRPYIYALLRDDSKIEEVKKITGERHGKIVRIVDVEK  (SEQ ID NO. 2)

VEKKFLGKPITVWKLYLEHPQDVPTIREKVREHPAVVDIFEYDIPFAKRYLIDKGLIPMEGEEELKILAF

DIETLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLVGQPLWDVSRSSTG

NLVEWFLLRKAYERNEVAPNKPSEEEYQRRLRESYTGGFVKEPEKGLWENIVYLDFRALYPSIIITHNVS

PDTLNLEGCKNYDIAPQVGHKFCKDIPGFIPSLLGHLLEERQKIKTKMKETQDPIEKILLDYRQKAIKLL

ANSFYGYYGYAKARWYCKECAESVTAWGRKYIELVWKELEEKFGFKVLYIDTDGLYATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS
```

Accordingly, preferred mutants according to the invention begin MAILDVDY or MLDVDY.

The inventors have found (see Example 1) that a uracil-binding pocket of the wild type polymerase forms part of the ssDNA template binding cleft of the polymerase (the so call cleft T). Furthermore the uracil-binding pocket comprises amino acids from two conserved regions of the polymerases: Region A and Region B separated by an unconserved region. In the archaeal polymerase from *Pyrococcus furiosus* (Pfu-Pol) Region A is formed by the amino acids 1-40 and Region B by amino acids 78-130. Highly conserved residues in these two regions form the highly ordered uracil-binding pocket. Other archaea have similar regions A & B in their respective polymerases as illustrated in FIG. 1. Preferably, one or more of the amino acids in Regions A and/or B are altered to form the variant archaeal DNA polymerase.

Figure 1:
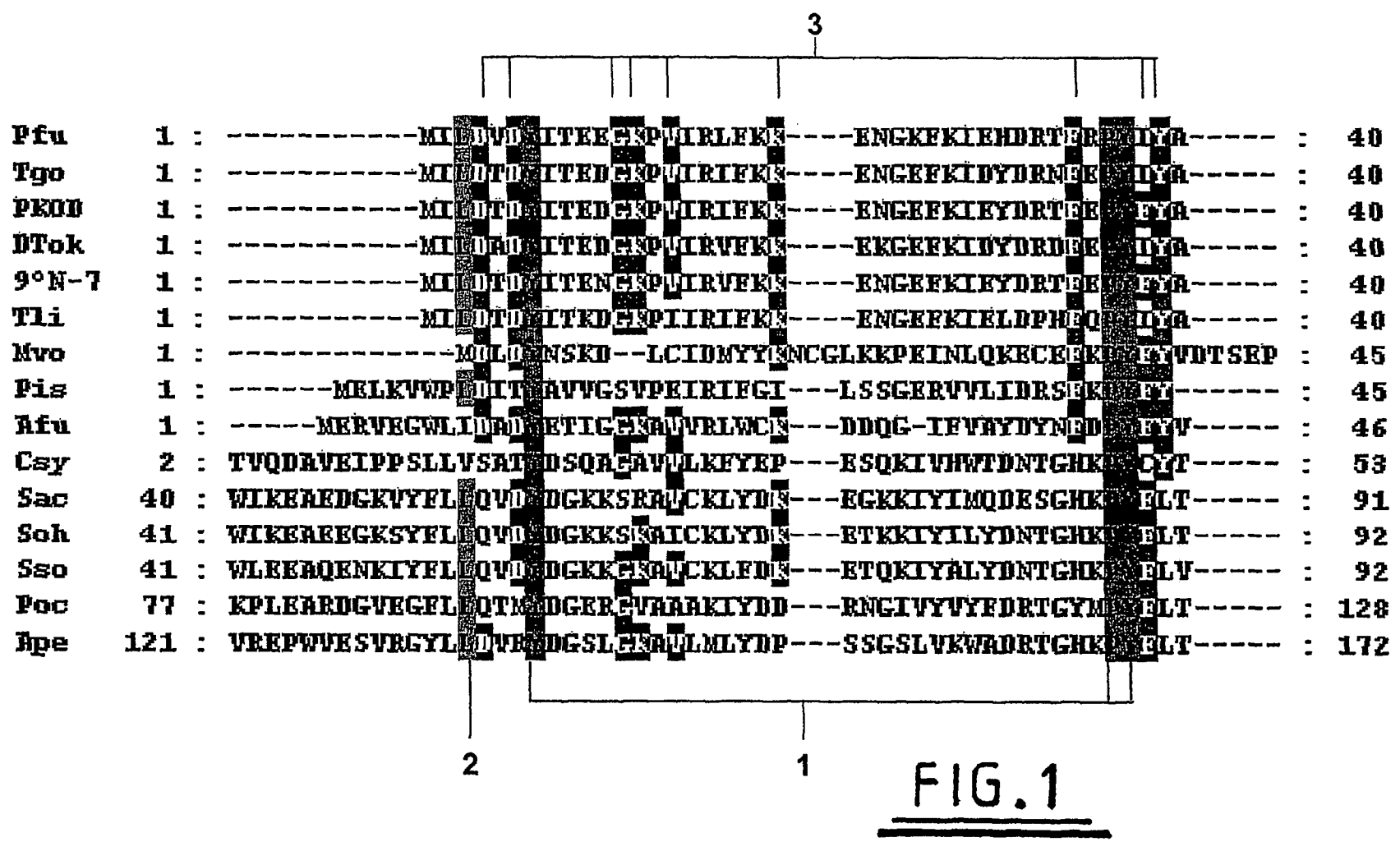
Figure 1:
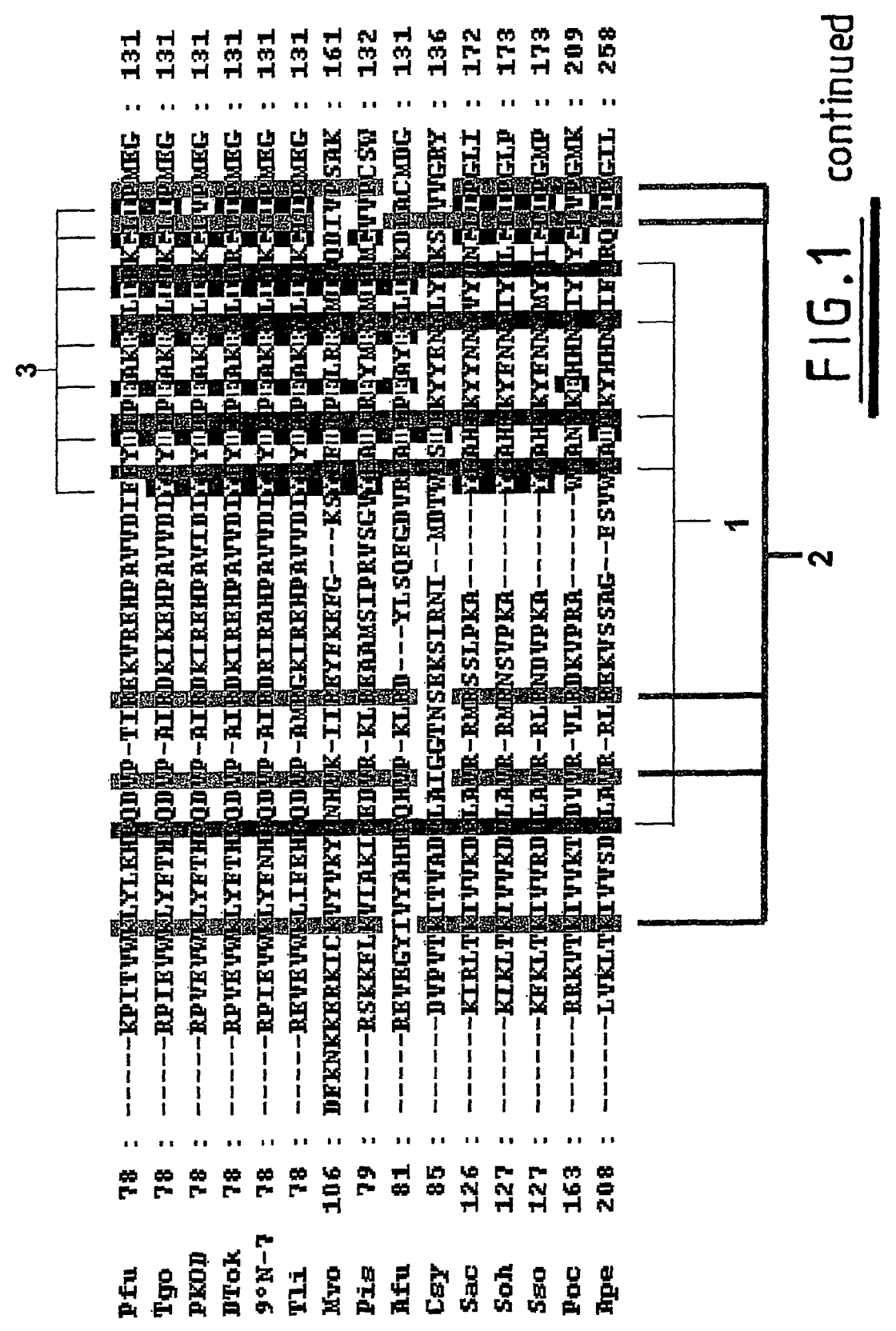

FIG. 1 illustrates a sequence alignment of the N-terminal domains of various archaeal polymerases. In FIG. 1 amino acids designated (1) have 90% or greater identity, (2) indicates 80-90% identity and (3) 60-80% identity. The two highly conserved regions that form the uracil binding pocket are:

Region A, amino acids 1-40 in Pfu-Pol (and corresponding regions in the other polymerases); and Region B, amino acids 78-131 in Pfu-Pol (and corresponding regions in the other polymerases).

It is preferred that the variant is formed by alteration of one of the amino acids block shaded (1, 2 or 3) in FIG. 1. For example the alteration may be in the motif: E - - I - F/Y - - - Y - - D.

The alteration may consist of a substitution, deletion or addition. One of the invariant residues may be altered or other residues in Regions A and/or B that affect the conformation of the uracil-binding pocket.

The inventors believe that residues 7, 36, 37, 90-97 and 112-119 in Pfu-Pol are particularly important for uracil binding. Preferably, at least one of these residues is altered to effect the conformation of the pocket and thereby reduce its uracil-binding ability. More preferably, the mutation in Pfu-Pol consists of a change in the amino acids Y7, Y37, V93, I114 or P115. More preferably, the change consists of Y7A, Y37A, V93Q, V93R, I114R, I114Q or P115Δ. A most preferred Pfu-Pol mutation is V93Q.

Examples of preferred Pfu-Pol variants have the following amino acid sequences:

(a) Pfu pol Y7A (Y8A) (SEQ ID NO. 3)
MAILDVDAITEEGKPVIRLFKKENGKFKIEHDRTFRPYIYALLRDDSKIEEVKKITGERHGKIVRIVDVEK
VEKKFLGKPITVWKLYLEHPQDVPTIREKVREHPAVVDIFEYDIPFAKRYLIDKGLIPMEGEEELKILAF
DIETLYHEGEEFGKGPIIMISYADENEAKVITWKNIDLPYVEVVSSEREMIKRFLRIIREKDPDIIVTYN
GDSFDFPYLAKRAEKLGIKLTIGRDGSEPKMQRIGDMTAVEVKGRIRFDLYHVITRTINLPTYTLEAVYE
AIFGKPKEKVYADEIAKAWESGENLERVAKYSMEDAKATYELGKEFLPMEIQLSRLVGQPLWDVSRSSTG
NLVEWFLLRKAYERNEVAPNKPSEEEYQRRLRESYTGGFVKEPEKGLWENIVYLDFRALYPSIIITHNVS
PDTLNLEGCKNYDIAPQVGHKFCKDIPGFIPSLLGHLLEERQKIKTKMKETQDPIEKILLDYRQKAIKLL
ANSFYGYYGYAKARWYCKECAESVTAWGRKYIELVWKELEEKFGFKVLYIDTDGLYATIPGGESEEIKKK
ALEFVKYINSKLPGLLELEYEGFYKRGFFVTKKRYAVIDEEGKVITRGLEIVRRDWSEIAKETQARVLET
ILKHGDVEEAVRIVKEVIQKLANYEIPPEKLAIYEQITRPLHEYKAIGPHVAVAKKLAAKGVKIKPGMVI
GYIVLRGDGPISNRAILAEEYDPKKHKYDAEYYIENQVLPAVLRILEGFGYRKEDLRYQKTRQVGLTSWL
NIKKS (b) Pfu pol Y37A (Y38A) (SEQ ID NO. 4)
MAILDVDYITEEGKPVIRLFKKENGKFKIEHDRTFRPAIYALLRDDSKIEEVKKITGERHGKIVRIVDVEK
VEKKFLGKPITVWKLYLEHPQDVPTIREKVREHPAVVDIFEYDIPFAKRYLIDKGLIPMEGEEELKILAF
DIETLYHEGEEFGKGPIIMISYADENEAKVITWKNIDLPYVEVVSSEREMIKRFLRIIREKDPDIIVTYN
GDSFDFPYLAKRAEKLGIKLTIGRDGSEPKMQRIGDMTAVEVKGRIHFDLYHVITRTINLPTYTLEAVYE
AIFGKPKEKVYADEIAKAWESGENLERVAKYSMEDAKATYELGKEFLPMEIQLSRLVGQPLWDVSRSSTG
NLVEWFLLRKAYERNEVAPNKPSEEEYQRRLRESYTGGFVKEPEKGLWENIVYLDFRALYPSIIITHNVS
PDTLNLEGCKNYDIAPQVGHKFCKDIPGFIPSLLGHLLEERQKIKTKMKETQDPIEKILLDYRQKAIKLL
ANSFYGYYGYAKARWYCKECAESVTAWGRKYIELVWKELEEKFGFKVLYIDTDGLYATIPGGESEEIKKK
ALEFVKYINSKLPGLLELEYEGFYKRGFFVTKKRYAVIDEEGKVITRGLEIVRRDWSEIAKETQARVLET
ILKHGDVEEAVRIVKEVIQKLANYEIPPEKLAIYEQITRPLHEYKAIGPHVAVAKKLAAKGVKIKPGMVI
GYIVLRGDGPISNRAILAEEYDPKKHKYDAEYYIENQVLPAVLRILEGFGYRKEDLRYQKTRQVGLTSWL
NIKKS (c) Pfu pol V93Q (V94Q) (SEQ ID NO. 5)
MAILDVDYITEEGKPVIRLFKKENGKFKIEHDRTFRPYIYALLRDDSKIEEVKKITGERHGKIVRIVDVEK
VEKKFLGKPITVWKLYLEHPQDQPTIREKVREHPAVVDIFEYDIPFAKRYLIDKGLIPMEGEEELKILAF
DIETLYHEGEEFGKGPIIMISYADENEAKVITWKNIDLPYVEVVSSEREMIKRFLRIIREKDPDIIVTYN
GDSFDFPYLAKRAEKLGIKLTIGRDGSEPKMQRIGDMTAVEVKGRIHFDLYHVITRTINLPTYTLEAVYE
AIFGKPKEKVYADEIAKAWESGENLERVAKYSMEDAKATYELGKEFLPMEIQLSRLVGQPLWDVSRSSTG
NLVEWFLLRKAYERNEVAPNKPSEEEYQRRLRESYTGGFVKEPEKGLWENIVYLDFRALYPSIIITHNVS
PDTLNLEGCKNYDIAPQVGHKFCKDIPGFIPSLLGHLLEERQKIKTKMKETQDPIEKILLDYRQKAIKLL
ANSFYGYYGYAKARWYCKECAESVTAWGRKYIELVWKELEEKFGFKVLYIDTDGLYATIPGGESEEIKKK
ALEFVKYINSKLPGLLELEYEGFYKRGFFVTKKRYAVIDEEGKVITRGLEIVRRDWSEIAKETQARVLET
ILKHGDVEEAVRIVKEVIQKLANYEIPPEKLAIYEQITRPLHEYKAIGPHVAVAKKLAAKGVKIKPGMVI
GYIVLRGDGPISNRAILAEEYDPKKHKYDAEYYIENQVLPAVLRILEGFGYRKEDLRYQKTRQVGLTSWL
NIKKS (d) Pfu pol V93R (V94R) (SEQ ID NO. 6)
MAILDVDYITEEGKPVIRLFKKENGKFKIEHDRTFRPYIYALLRDDSKIEEVKKITGERHGKIVRIVDVEK
VEKKFLGKPITVWKLYLEHPQDRPTIREKVREHPAVVDIFEYDIPFAKRYLIDKGLIPMEGEEELKILAF
DIETLYHEGEEFGKGPIIMISYADENEAKVITWKNIDLPYVEVVSSEREMIKRFLRIIREKDPDIIVTYN
GDSFDFPYLAKRAEKLGIKLTIGRDGSEPKMQRIGDMTAVEVKGRIHFDLYEVITRTINLPTYTLEAVYE
AIFGKPKEKVYADEIAKAWESGENLERVAKYSMEDAKATYELGKEFLPMEIQLSRLVGQPLWDVSRSSTG
NLVEWFLLRKAYERNEVAPNKPSEEEYQRRLRESYTGGFVKEPEKGLWENIVYLDFRALYPSIIITHNVS
PDTLNLEGCKNYDIAPQVGHKFCKDIPGFIPSLLGHLLEERQKIKTKMKETQDPIEKILLDYRQKAIKLL
ANSFYGYYGYAKARWYCKECAESVTAWGRKYIELVWKELEEKFGFKVLYIDTDGLYATIPGGESEEIKKK
ALEFVKYINSKLPGLLELEYEGFYKRGFFVTKKRYAVIDEEGKVITRGLEIVRRDWSEIAKETQARVLET
ILKHGDVEEAVRIVKEVIQKLANYEIPPEKLAIYEQITRPLHEYKAIGPHVAVAKKLAAKGVKIKPGMVI
GYIVLRGDGPISNRAILAEEYDPKKEKYDAEYYIENQVLPAVLRILEGFGYRKEDLRYQKTRQVGLTSWL
NIKKS (e) Pfu pol I114R (I115R) (SEQ ID NO. 7)
MAILDVDAITEEGKPVIRLFKKENGKFKIEHDRTFRPYIYALLRDDSKIEEVKKITGERHGKIVRIVDVEK
VEKKFLGKPITVWKLYLEHPQDVPTIREKVREHPAVVDIFEYDRPFAKRYLIDKGLIPMEGEEELKILAF
DIETLYHEGEEFGKGPIIMISYADENEAKVITWKNIDLPYVEVVSSEREMIKRFLRIIREKDPDIIVTYN
GDSFDFPYLAKRAEKLGIKLTIGRDGSEPKMQRIGDMTAVEVKGRIHFDLYHVITRTINLPTYTLEAVYE
AIFGKPKEKVYADEIAKAWESGENLERVAKYSMEDAKATYELGKEFLPMEIQLSRLVGQPLWDVSRSSTG
NLVEWFLLRKAYERNEVAPNKPSEEEYQRRLRESYTGGFVKEPEKGLWENIVYLDFRALYPSIIITHNVS
PDTLNLEGCKNYDIAPQVGHKFCKDIPGFIPSLLGHLLEERQKIKTKMKETQDPIEKILLDYRQKAIKLL
ANSFYGYYGYAKARWYCKECAESVTAWGRKYIELVWKELEEKFGFKVLYIDTDGLYATIPGGESEEIKKK
ALEFVKYINSKLPGLLELEYEGFYKRGFFVTKKRYAVIDEEGKVITRGLEIVRRDWSEIAKETQARVLET
ILKEGDVEEAVRIVKEVIQKLANYEIPPEKLAIYEQITRPLHEYKAIGPHVAVAKKLAAKGVKIKPGMVI
GYIVLRGDGPISNRAILAEEYDPKKHKYDAEYYIENQVLPAVLRILEGFGYRKEDLRYQKTRQVGLTSWL
NIKKS (f) Pfu pol I114Q (I115Q) (SEQ ID NO. 8)
MAILDVDYITEEGKPVIRLFKKENGKFKIEHDRTFRPAIYALLRDDSKIEEVKKITGERHGKIVRIVDVEK
VEKKFLGKPITVWKLYLEHPQDVPTIREKVREHPAVVDIFEYDQPFAKRYLIDKGLIPMEGEEELKILAF
DIETLYHEGEEFGKGPIIMISYADENEAKVITWKNIDLPYVEVVSSEREMIKRFLRIIREKDPDIIVTYN
GDSFDFPYLAKRAEKLGIKLTIGRDGSEPKMQRIGDMTAVEVKGRIHFDLYHVITRTINLPTYTLEAVYE
AIFGKPKEKVYADEIAKAWESGENLERVAKYSMEDAKATYELGKEFLPMEIQLSRLVGQPLWDVSRSSTG
NLVEWFLLRKAYERNEVAPNKPSEEEYQRRLRESYTGGFVKEPEKGLWENIVYLDFRALYPSIIITENVS
PDTLNLEGCKNYDIAPQVGEKFCKDIPGFIPSLLGHLLEERQKIKTKMKETQDPIEKILLDYRQKAIKLL

```
ANSFYGYYGYAKARWYCKECAESVTAWGRKYIELVWKELEEKFGFKVLYIDTDGLYATIPGGESEEIKKK
ALEFVKYINSKLPGLLELEYEGFYKRGFFVTKKRYAVIDEEGKVITRGLEIVRRDWSEIAKETQARVLET
ILKHGDVEEAVRIVKEVIQKLANYEIPPEKLAIYEQITRPLHEYKAIGPHVAVAKKLAAKGVKIKPGMVI
GYIVLRGDGPISNRAILAEEYDPKKHKYDAEYYIENQVLPAVLRILEGFGYRKEDLRYQKTRQVGLTSWL
NIKKS
```

It will be appreciated that the preferred mutants listed above comprise an alanine (A) insertion at position 2 which is not found in the wild type. Accordingly such mutants may be designated Y8A, Y38A, V94Q, V94R, I115R and I115Q mutants of the MAILDVDY form of Pfu Pol and correspond to Y7A, Y37A, V93Q, V93R, I114R and I114Q mutants of the true wild-type (MILDVDY). Y7A, Y37A, V93Q, V93R, I114R and I114Q mutants of the true wild-type (MILDVDY) are also preferred mutants according to the invention.

It will be appreciated that equivalent residues in other archaeal polymerases may be mutated (see FIG. 1). For instance Y7A, Y37A, V93Q, V93R, I114R, I114Q and P115Δ remain preferred mutants in Tgo-pol, DTok-pol and 9°N-7-pol.

The present invention also provides nucleic acids encoding an archaeal DNA polymerase variant as defined above.

Examples of preferred mutant genes have the following DNA sequences:

```
(a) Pfu pol Y7A (Y8A)
ATGGCTATCCTGGACGTTGACGCCATCACCGAAGAAGGTAAGCCGGTTATCCGTCTGTTCAAAAAAGAAAACGGT    (SEQ ID NO. 9)
AAATTCAAAATCGAACACGACCGTACCTTCCGTCCGTACATCTACGCTCTGCTGCGTGACGACTCTAAAATCGAA
GAAGTTAAAAAAATCACCGGTGAACGTCATGGAAAGATTGTGAGAATTGTTGATGTAGAGAAGGTTGAGAAAAAG
TTTCTCGGCAAGCCTATTACCGTGTGGAAACTTTATTTGGAACATCCCCAAGATGTTCCCACTATTAGAGAAAAA
GTTAGAGAACATCCAGCAGTTGTGGACATCTTCGAATACGATATTCCATTTGCAAAGAGATACCTCATCGACAAA
GGCCTAATACCAATGGAGGGGGAAGAAGAGCTAAAGATTCTTGCCTTCGATATAGAAACCCTCTATCACGAAGGA
GAAGAGTTTGGAAAAGGCCCAATTATAATGATTAGTTATGCAGATGAAAATGAAGCAAAGGTGATTACTTGGAAA
AACATAGATCTTCCATACGTTGAGGTTGTATCAAGCGAGAGAGAGATGATAAAGAGATTTCTCAGGATTATCAGG
GAGAAGGATCCTGACATTATAGTTACTTATAATGGAGACTCATTCGACTTCCCATATTTAGCGAAAAGGGCAGAA
AAACTTGGGATTAAATTAACCATTGGAAGAGATGGAAGCGAGCCCAAGATGCAGAGAATAGGCGATATGACGGCT
GTAGAAGTCAAGGGAAGAATACATTTCGACTTGTATCATGTAATAACAAGGACAATAAATCTCCCAACATACACA
CTAGAGGCTGTATATGAAGCAATTTTTGGAAAGCCAAAGGAGAAGGTATACGCCGACGAGATAGCAAAAGCCTGG
GAAAGTGGAGAGAACCTTGAGAGAGTTGCCAAATACTCGATGGAAGATGCAAAGGCAACTTATGAACTCGGGAAA
GAATTCCTTCCAATGGAAATTCAGCTTTCAAGATTAGTTGGACAACCTTTATGGGATGTTTCAAGGTCAAGCACA
GGGAACCTTGTAGAGTGGTTCTTACTTAGGAAAGCCTACGAAAGAAACGAAGTAGCTCCAAACAAGCCAAGTGAA
GAGGAGTATCAAAGAAGGCTCAGGGAGAGCTACACAGGTGGATTCGTTAAAGAGCCAGAAAAGGGGTTGTGGGAA
AACATAGTATACCTAGATTTTAGAGCCCTATATCCCTCGATTATAATTACCCACAATGTTTCTCCCGATACTCTA
AATCTTGAGGGATGCAAGAACTATGATATCGCTCCTCAAGTAGGCCACAAGTTCTGCAAGGACATCCCTGGTTTT
ATACCAAGTCTCTTGGGACATTTGTTAGAGGAAAGACAAAAGATTAAGACAAAAATGAAGGAAACTCAAGATCCT
ATAGAAAAAATACTCCTTGACTATAGACAAAAAGCGATAAAACTCTTAGCAAATTCTTTCTACGGATATTATGGC
TATGCAAAAGCAAGATGGTACTGTAAGGAGTGTGCTGAGAGCGTTACTGCCTGGGGAAGAAAGTACATCGAGTTA
GTATGGAAGGAGCTCGAAGAAAAGTTTGGATTTAAAGTCCTCTACATTGACACTGATGGTCTCTATGCAACTATC
CCAGGAGGAGAAAGTGAGGAAATAAAGAAAAAGGCTCTAGAATTTGTAAAATACATAAATTCAAAGCTCCCTGGA
CTGCTAGAGCTTGAATATGAAGGGTTTTATAAGAGGGGATTCTTCGTTACGAAGAAGAGGTATGCAGTAATAGAT
GAAGAAGGAAAAGTCATTACTCGTGGTTTAGAGATAGTTAGGAGAGATTGGAGTGAAATTGCAAAAGAAACTCAA
GCTAGAGTTTTGGAGACAATACTAAAACACGGAGATGTTGAAGAAGCTGTGAGAATAGTAAAAGAAGTAATACAA
AAGCTTGCCAATTATGAAATTCCACCAGAGAAGCTCGCAATATATGAGCAGATAACAAGACCATTACATGAGTAT
AAGGCGATAGGTCCTCACGTAGCTGTTGCAAAGAAACTAGCTGCTAAAGGAGTTAAAATAAAGCCAGGAATGGTA
ATTGGATACATAGTACTTAGAGGCGATGGTCCAATTAGCAATAGGGCAATTCTAGCTGAGGAATACGATCCCAAA
AAGCACAAGTATGACGCAGAATATTACATTGAGAACCAGGTTCTTCCAGCGGTACTTAGGATATTGGAGGGATTT
GGATACAGAAAGGAAGACCTCAGATACCAAAAGACAAGACAAGTCGGCCTAACTTCCTGGCTTAACATTAAAAAA
TCC (b) Pfu pol V93Q (V94Q)
ATGGCTATCCTGGACGTTGACTACATCACCGAAGAAGGTAAGCCGGTTATCCGTCTGTTCAAAAAAGAAAACGGT    (SEQ ID NO. 10)
AAATTCAAAATCGAACACGACCGTACCTTCCGTCCGTACATCTACGCTCTGCTGCGTGACGACTCTAAAATCGAA
GAAGTTAAAAAAATCACCGGTGAACGTCATGGAAAGATTGTGAGAATTGTTGATGTAGAGAAGGTTGAGAAAAAG
TTTCTCGGCAAGCCTATTACCGTGTGGAAACTTTATTTGGAACATCCCCAAGATCAGCCCACTATTAGAGAAAAA
GTTAGAGAACATCCAGCAGTTGTGGACATCTTCGAATACGATATTCCATTTGCAAAGAGATACCTCATCGACAAA
GGCCTAATACCAATGGAGGGGGAAGAAGAGCTAAAGATTCTTGCCTTCGATATAGAAACCCTCTATCACGAAGGA
GAAGAGTTTGGAAAAGGCCCAATTATAATGATTAGTTATGCAGATGAAAATGAAGCAAAGGTGATTACTTGGAAA
AACATAGATCTTCCATACGTTGAGGTTGTATCAAGCGAGAGAGAGATGATAAAGAGATTTCTCAGGATTATCAGG
GAGAAGGATCCTGACATTATAGTTACTTATAATGGAGACTCATTCGACTTCCCATATTTAGCGAAAAGGGCAGAA
AAACTTGGGATTAAATTAACCATTGGAAGAGATGGAAGCGAGCCCAAGATGCAGAGAATAGGCGATATGACGGCT
GTAGAAGTCAAGGGAAGAATACATTTCGACTTGTATCATGTAATAACAAGGACAATAAATCTCCCAACATACACA
CTAGAGGCTGTATATGAAGCAATTTTTGGAAAGCCAAAGGAGAAGGTATACGCCGACGAGATAGCAAAAGCCTGG
GAAAGTGGAGAGAACCTTGAGAGAGTTGCCAAATACTCGATGGAAGATGCAAAGGCAACTTATGAACTCGGGAAA
GAATTCCTTCCAATGGAAATTCAGCTTTCAAGATTAGTTGGACAACCTTTATGGGATGTTTCAAGGTCAAGCACA
GGGAACCTTGTAGAGTGGTTCTTACTTAGGAAAGCCTACGAAAGAAACGAAGTAGCTCCAAACAAGCCAAGTGAA
GAGGAGTATCAAAGAAGGCTCAGGGAGAGCTACACAGGTGGATTCGTTAAAGAGCCAGAAAAGGGGTTGTGGGAA
AACATAGTATACCTAGATTTTAGAGCCCTATATCCCTCGATTATAATTACCCACAATGTTTCTCCCGATACTCTA
AATCTTGAGGGATGCAAGAACTATGATATCGCTCCTCAAGTAGGCCACAAGTTCTGCAAGGACATCCCTGGTTTT
ATACCAAGTCTCTTGGGACATTTGTTAGAGGAAAGACAAAAGATTAAGACAAAAATGAAGGAAACTCAAGATCCT
ATAGAAAAAATACTCCTTGACTATAGACAAAAAGCGATAAAACTCTTAGCAAATTCTTTCTACGGATATTATGGC
TATGCAAAAGCAAGATGGTACTGTAAGGAGTGTGCTGAGAGCGTTACTGCCTGGGGAAGAAAGTACATCGAGTTA
GTATGGAAGGAGCTCGAAGAAAAGTTTGGATTTAAAGTCCTCTACATTGACACTGATGGTCTCTATGCAACTATC
CCAGGAGGAGAAAGTGAGGAAATAAAGAAAAAGGCTCTAGAATTTGTAAAATACATAAATTCAAAGCTCCCTGGA
CTGCTAGAGCTTGAATATGAAGGGTTTTATAAGAGGGGATTCTTCGTTACGAAGAAGAGGTATGCAGTAATAGAT
GAAGAAGGAAAAGTCATTACTCGTGGTTTAGAGATAGTTAGGAGAGATTGGAGTGAAATTGCAAAAGAAACTCAA
GCTAGAGTTTTGGAGACAATACTAAAACACGGAGATGTTGAAGAAGCTGTGAGAATAGTAAAAGAAGTAATACAA
```

-continued

AAGCTTGCCAATTATGAAATTCCACCAGAGAAGCTCGCAATATATGAGCAGATAACAAGACCATTACATGAGTAT
AAGGCGATAGGTCCTCACGTAGCTGTTGCAAAGAAACTAGCTGCTAAAGGAGTTAAAATAAAGCCAGGAATGGTA
ATTGGATACATAGTACTTAGAGGCGATGGTCCAATTAGCAATAGGGCAATTCTAGCTGAGGAATACGATCCCAAA
AAGCACAAGTATGACGCAGAATATTACATTGAGAACCAGGTTCTTCCAGCGGTACTTAGGATATTGGAGGGATTT
GGATACAGAAAGGAAGACCTCAGATACCAAAAGACAAGACAAGTCGGCCTAACTTCCTGGCTTAACATTAAAAAA
TCC (c) Pfu Pol P115Δ (P116Δ)

ATGGCTATCCTGGACGTTGACTACATCACCGAAGAAGGTAAGCCGGTTATCCGTCTGTTCAAAAAAGAAAACGGT  (SEQ ID NO. 11)
AAATTCAAAATCGAACACGACCGTACCTTCCGTCCGTACATCTACGCTCTGCTGCGTGACGACTCTAAAATCGAA
GAAGTTAAAAAAATCACCGGTGAACGTCATGGAAAGATTGTGAGAATTGTTGATGTAGAGAAGGTTGAGAAAAAG
TTTCTCGGCAAGCCTATTACCGTGTGGAAACTTTATTTGGAACATCCCCAAGATGTTCCCACTATTAGAGAAAAA
GTTAGAGAACATCCAGCAGTTGTGGACATCTTCGAATACGATATTTTTGCAAAGAGATACCTCATCGACAAAGGC
CTAATACCAATGGAGGGGGAAGAAGAGCTAAAGATTCTTGCCTTCGATATAGAAACCCTCTATCACGAAGGAGAA
GAGTTTGGAAAAGGCCCAATTATAATGATTAGTTATGCAGATGAAAATGAAGCAAAGGTGATTACTTGGAAAAAC
ATAGATCTTCCATACGTTGAGGTTGTATCAAGCGAGAGAGAGATGATAAAGAGATTTCTCAGGATTATCAGGGAG
AAGGATCCTGACATTATAGTTACTTATAATGGAGACTCATTCGACTTCCCATATTTAGCGAAAAGGGCAGAAAAA
CTTGGGATTAAATTAACCATTGGAAGAGATGGAAGCGAGCCCAAGATGCAGAGAATAGGCGATATGACGGCTGTA
GAAGTCAAGGGAAGAATACATTTCGACTTGTATCATGTAATAACAAGGACAATAAATCTCCCAACATACACACTA
GAGGCTGTATATGAAGCAATTTTTGGAAAGCCAAAGGAGAAGGTATACGCCGACGAGATAGCAAAAGCCTGGGAA
AGTGGAGAGAACCTTGAGAGAGTTGCCAAATACTCGATGGAAGATGCAAAGGCAACTTATGAACTCGGGAAAGAA
TTCCTTCCAATGGAAATTCAGCTTTCAAGATTAGTTGGACAACCTTTATGGGATGTTTCAAGGTCAAGCACAGGG
AACCTTGTAGAGTGGTTCTTACTTAGGAAAGCCTACGAAAGAAACGAAGTAGCTCCAAACAAGCCAAGTGAAGAG
GAGTATCAAAGAAGGCTCAGGGAGAGCTACACAGGTGGATTCGTTAAAGAGCCAGAAAAGGGGTTGTGGGAAAAC
ATAGTATACCTAGATTTTAGAGCCCTATATCCCTCGATTATAATTACCCACAATGTTTCTCCCGATACTCTAAAT
CTTGAGGGATGCAAGAACTATGATATCGCTCCTCAAGTAGGCCCACAAGTTCTGCAAGGACATCCCTGGTTTTATA
CCAAGTCTCTTGGGACATTTGTTAGAGGAAAGACAAAAGATTAAGACAAAAATGAAGGAAACTCAAGATCCTATA
GAAAAAATACTCCTTGACTATAGACAAAAAGCGATAAAACTCTTAGCAAATTCTTTCTACGGATATTATGGCTAT
GCAAAAGCAAGATGGTACTGTAAGGAGTGTGCTGAGAGCGTTACTGCCTGGGGAAGAAAGTACATCGAGTTAGTA
TGGAAGGAGCTCGAAGAAAAGTTTGGATTTAAAGTCCTCTACACTGATGGTCTCTATGCAACTATCCCA
GGAGGAGAAAGTGAGGAAATAAAGAAAAAGGCTCTAGAATTTGTAAAATACATAAATTCAAAGCTCCCTGGACTG
CTAGAGCTTGAATATGAAGGGTTTTATAAGAGGGGATTCTTCGTTACGAAGAAGAGGTATGCAGTAATAGATGAA
GAAGGAAAAGTCATTACTCGTGGTTTAGAGATAGTTAGGAGAGATTGGAGTGAAATTGCAAAAGAAACTCAAGCT
AGAGTTTTGGAGACAATACTAAAACACGGAGATGTTGAAGAAGCTGTGGAGAAGTAGTAAAAGAAGTAATACAAAAG
CTTGCCAATTATGAAATTCCACCAGAGAAGCTCGCAATATATGAGCAGATAACAAGACCATTACATGAGTATAAG
GCGATAGGTCCTCACGTAGCTGTTGCAAAGAAACTAGCTGCTAAAGGAGTTAAAATAAAGCCAGGAATGGTAATT
GGATACATAGTACTTAGAGGCGATGGTCCAATTAGCAATAGGGCAATTCTAGCTGAGGAATACGATCCCAAAAAG
CACAAGTATGACGCAGAATATTACATTGAGAACCAGGTTCTTCCAGCGGTACTTAGGATATTGGAGGGATTTGGA
TACAGAAAGGAAGACCTCAGATACCAAAAGACAAGACAAGTCGGCCTAACTTCCTGGCTTAACATTAAAAAATCC

It will be appreciated that preferred mutants encoded by the DNA sequences listed above comprise a codon for an alanine (A) inserted at position 2 that is not found in the wild type. Accordingly such mutants may be designated Y8A, Y38A and P116Δ mutants of the MAILDVDY form of Pfu Pol and correspond to Y7A, Y37A and P115Δ mutants of the true wild-type (MILDVDY).

It will also be appreciated that DNA sequences for other preferred mutants will be readily apparent given the above-mentioned amino acid sequences. Accordingly DNA molecules encoding Y7A, Y37A, V93A, I114R, I114Q and P115Δ mutants of the true wild-type (MILDVDY) are also preferred nucleic acids according to the invention.

The variant polymerases as defined above are particularly useful for PCRs since they are thermally stable, have proof-reading ability but are not stalled by the presence of dUTP.

Accordingly, a further aspect of the present invention provides a kit useful for polymerase chain reactions comprising DNA to be amplified, free bases, primers and a variant archaeal DNA polymerase having a modified amino acid sequence of a wild-type amino acid sequence, the modified sequence being in the amino-terminal amino acids that comprise a uracil binding pocket in the wild-type polymerase whereby the variant polymerase has reduced affinity for uracil compared to the wild-type polymerase.

The present invention further provides a method of amplifying DNA comprising the steps of (i) denaturing a double strand of DNA by heating a solution containing the DNA, free oligonucleotides, primers and a variant archaeal DNA polymerase having a modified amino acid sequence of a wild-type amino acid sequence, the modified sequence being in the amino-terminal amino acids that comprise a uracil binding pocket in the wild type polymerase whereby the variant polymerase has reduced affinity for uracil compared to the wild-type polymerase; (ii) reducing the temperature of the solution to effect annealing of the primer and the DNA and (iii) heating the solution to effect extension of DNA by the variant polymerase.

The ability of the variant DNA polymerase to amplify DNA in the presence of dUTP results in it being particularly suitable for PCR that uses dUTP rather than dTTP, for example in the prevention of contamination of samples.

A preferred protocol for carrying out PCR utlising variant polymerases according to the method of the present invention is as follows: PCR may carried out under the following conditions: 100 μl volume, 20 mM Tris-HCl pH 8.8, 10 mM KCl, 10 mM $(NH_4)_2 SO_4$, 2 mM $MgSO_4$, 0.1% Triton X100, 100 μg/ml BSA, 250 μM each of dATP, dGTP, dCTP and either 250 μM dTTP or 250 μM dUTP, 2.5 units DNA polymerase overlayed with 40 μl of mineral oil (1 unit of polymerase is defined as amount of enzyme that incorporates 10 nmol of dATP into acid-precipitable material using an activated calf-thymus DNA-based assay (4) in 30 min at 72° C.). 5 ng of template DNA to be amplified is used and the concentration of the forward and reverse primers (each 18 bases in length) is 0.3 μM. Each PCR consisted of 30 cycles of 1 min at 95° C., 2 min at 52° C. and 4.5 min at 72° C.

The present invention will now be further illustrated by means of the following Examples in which Example 1 investigates the uracil-binding pocket of Archaea polymerases, in particular the hyperthermophilic archaea, *Pyrococcus furiosus* (Pfu-pol) and Example 2 investigates the effect of mutagenesis of residues in and around the uracil-binding pocket of archaeal DNA polymerases, and with reference to the accompanying drawings in which:—

FIG. 1 illustrates an amino acid sequence alignment of archaeal family B DNA polymerases, corresponding to residues 1-130 of *Pyrococcus furiosus* polymerase. Candidates were identified using a WUBLAST search (European Bioinformatics Institute, http://www.ebi.ac.uk/ebi_home.html) for homologues of Pfu-Pol. An additional ENTREZ search of the SWISSPROT database for family B DNA polymerises polymerases was performed (Genbank, http://www.ncbi.nlm.nih.gov/). Sequence alignments were generated using ClustalX (version 1.81) [J. D. Thompson et al., *Nucl. Acids. Res* 24, 4876 (1997)]. The organisms and the DNA polymerase sequence accession numbers were: *Pyrococcus furiosus* (Pfu) (SEQ ID NO: 18) (P80061), *Thermococcus gorgonarius* (Tgo) (SEQ ID NO: 19) (pdb 1D5A), *Pyrococcus kodakaraensis* (PKOD) (SEQ ID NO: 20) (gi/13399597), *Desulfurococcus* strain Tok (DTok) (SEQ ID NO: 21), *Thermococcus* sp. 9° N-7 (9° N-7) (SEQ ID NO: 22) (Q56366), *Thermococcus litoralis* (Tli) (SEQ ID NO: 23) (AAA72101.1), *Methanococcus voltae* (Mvo) (SEQ ID NO: 24) (P52025), *Pyrobaculum islandicum* (Pis) (SEQ ID NO: 25) (AAF27815.1), *Archaeoglobus fulgidus* (Afu) (SEQ ID NO: 26) (O29753), *Cenarchaeaum symbiosum* (Csy) (SEQ ID NO: 27) (AAC62712.1), *Sulfolobus acidocaldarius* (Sac) (SEQ ID NO: 28) (P95690) *Sulfurisphaera ohwakuensis* (Soh) (SEQ ID NO: 29) (BAA23994.1), *Sulfolobus solfataricus* (Sso) (SEQ ID NO: 30) (P26811), *Pyrodictium occultum* (Poc) (SEQ ID NO: 31) (BAA07579.1) and *Aeropyrum pernix* (Ape) (SEQ ID NO: 32) (NP_148473.1).

FIG. 2A: The template-binding cleft T (21) of Tgo-Pol showing the presence of a pocket. B: The N-terminal domain of Tgo-Pol (SEQ ID NO:12) with amino acids that form the pocket shown in space-till: Y7; P36/Y37; amino acids 90-97 (22); amino acids 112-116 (23). α-Helices are shown (24) and β-sheets (25). C: Amino acid sequences of the N-terminal domains of Tgo-Pol (upper sequence (SEQ ID NO.12)) and RB69-Pol (lower sequence (SEQ ID NO. 13)). Amino acids that form the pocket in Tgo-Pol (and the corresponding residues in RB69-Pol) are underlined and correspond to the amino acids identified in panels B and E. Cylinders represent α-helices and arrows β-sheets. The amino acid sequences have minimal homology and have been aligned using structural homology. D: Structural alignment of the N-terminal domains of Tgo-Pol (SEQ ID NO:12) and RB69-Pol (SEQ ID NO:13). The insert in Tgo-Pol is shown (26). This structural superimposition was used to generate the amino acid alignment shown in C. E: The N-terminal domain of RB69-Pol (SEQ ID NO:13). Space-filled amino acids (V8 Q10; residues 65-72 (27); residues 84-89 (28); P35/S36 lie substantially behind residues 84-89) correspond to those in Tgo-Pol (shown in panel B) which form the pocket. Both V8 and Q10 are near the position of the Tgo-Pol Y7. α-Helices are shown (24) and β-sheets (25). Images/structural homology models were produced using Swiss-Model [N. Guex, M. C. Peitsch, *Electrophoresis* 18, 2714 (1997)] (http://www.expasy.ch/spdbv/), POV-Ray [C. Cason, POV-Ray for Windows, version 3.1 g (1999)] (http://www.povray.org) and Rasmol [R. Sayle, J. F. Milner-White, *Trends Biochem. Sci.* 20, 374 (1995)].

Figure 3:
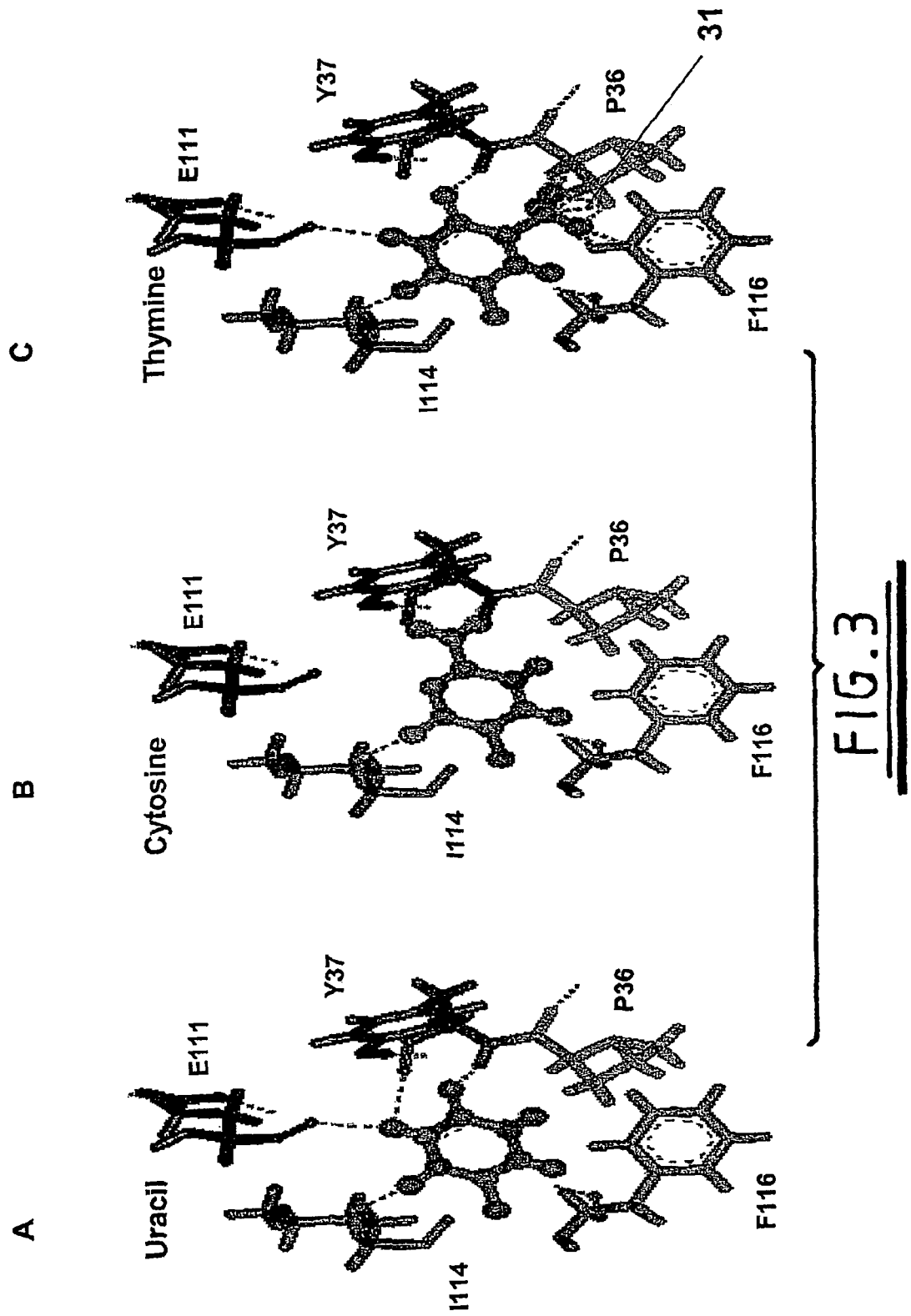

FIG. 3: Modelling pyrimidines into the N-terminal domain pocket of Tgo-Pol using Web Lab Viewer Pro [Molecular Simulations Inc., Web Lab Viewer Pro (version 4.0) (2000)] (http://www.msi.com). Hatched lines represent hydrogen bonds; except steric clashes are identified (31). Uracil formed four enzyme-base hydrogen bonds and no clashes. Cytosine and thymine resulted in fewer hydrogen bonds and/or clashes.

Figure 4:
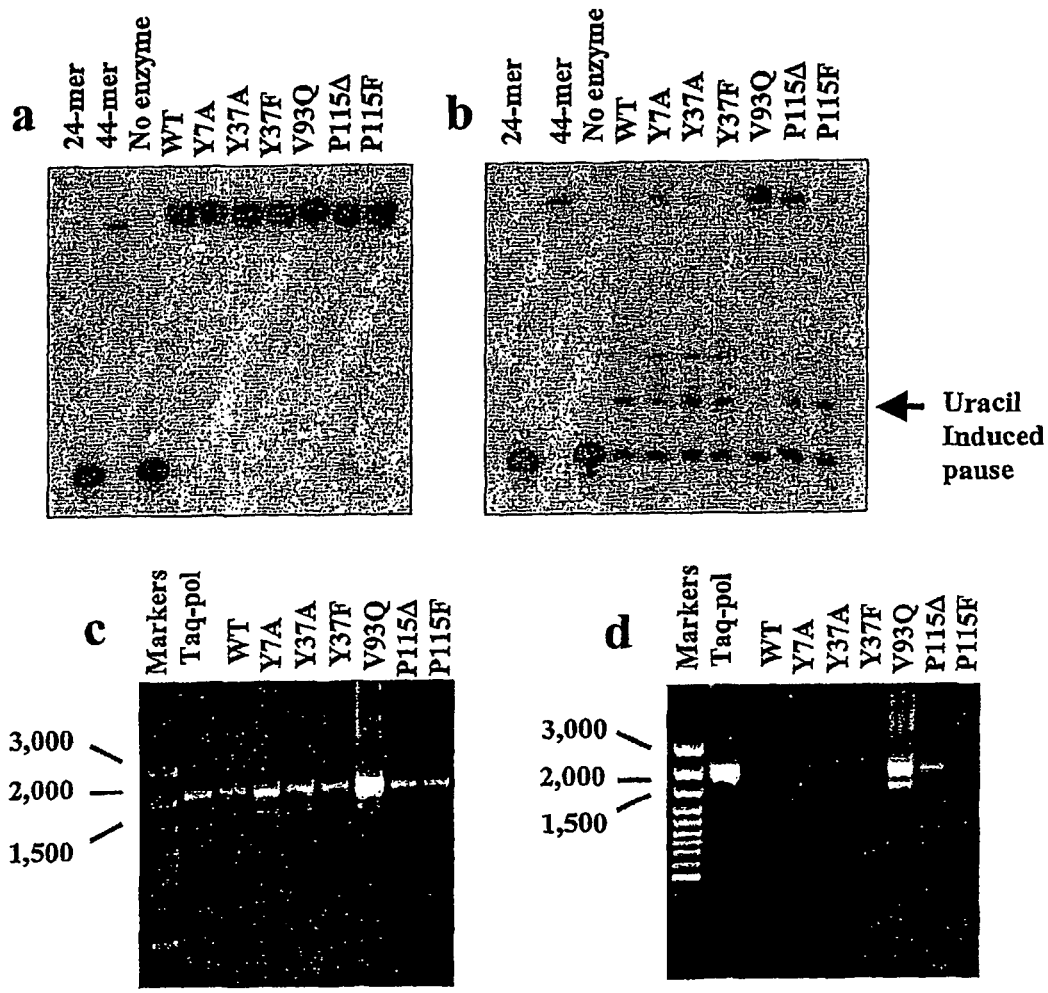

FIGS. 4 A and B: Primer extension reactions using a 5'-$^{32}$P labeled 24-mer primer (5'-GGGGATCCTCTAGAGTCGAC-CTGC-3' (SEQ ID NO.14)) (2.5 nM) annealed to 44-mer template (5'-GGAGACAAGCTTG(U/T)ATGCCT GCAGGTCGACTCTAGCGGCTAAAA-3' (SEQ ID NO.15)) (5 nM). The primer hybridises with the underlined section of the template to place a uracil (thymine in controls) seven bases from the primer-template junction (H. H. Hogrefe, C. J. Hansen, B. R. Scott, K. B. Nielson, *Proc. Natl. Acad. Sci. U.S.A.*, 99, 596 (2002)). In the presence of the four dNTPs all Pfu-Pol variants were able to fully copy the control template, lacking uracil, converting the labeled 24-mer primer into a product 44 bases long (A). With uracil in the template the wild-type enzyme (WT) stalled polymerisation (H. H. Hogrefe, C. J. Hansen, B. R. Scott, K. B. Nielson, *Proc. Natl. Acad. Sci. U.S.A.*, 99, 596 (2002)) giving a truncated product (B). The arrow (41) indicates the major pause site, shown (using standards, not illustrated) to occur four base before uracil. With Y7A, V93Q and P115Δ some full-length product was observed (amounts: V93Q>P115Δ>Y7A) indicating read-through of the template-strand uracil (panel B). No full-length product was seen with Y37A, Y37F and P115F (some material partially extended past the "uracil induced pause" was seen with Y7A, Y37A and Y37F. The first and second lanes contain standard 24-mer and 44-mer. C and D: PCR reactions. In control PCR with the four normal dNTPs (dATP, dGTP, dCTP and dTTP) all the Pfu-Pol variants (and Taq-Pol) gave the anticipated PCR product, ~2 kbases in length (C). When dUTP replaced dTTP, Taq-Pol produced a 2 kbase fragment (D). With most Pfu-Pol variants (WT, Y37A, Y37F and P115F) no PCR product was seen (D). Three Pfu-Pol mutant's produced a PCR product (amounts: V93Q>P115Δ>Y7A) (2× and 4× loadings, respectively, were used for visualisation with P115Δ and Y7A). All PCR reactions were carried out under identical conditions with no optimisation; this probably accounts for the lower weight contaminant seen in some lanes. Markers (important sizes indicated) were from Promega.

Figure 5:
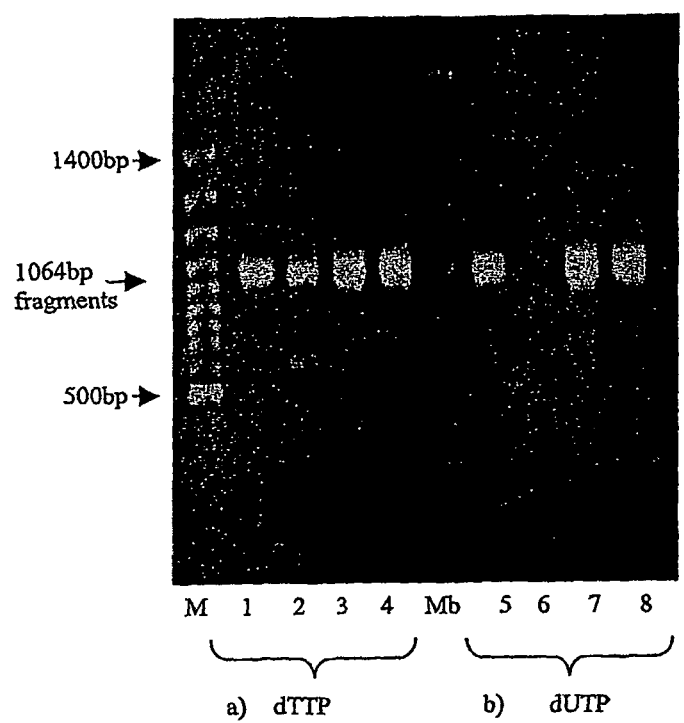

FIG. 5: Polymerase chain reaction (PCR) with *Thermus aquaticus* polymerase (Taq-Pol) and *Pyrococcus furiosus* polymerase (Pfu-Pol) (wild type and two mutants, V93Q and V93R). A DNA fragment (~1 kilobase in length) from the plasmid pET-17b(Pfu-Pol) was amplified. Conditions 20 mM Tris-HCl, pH 8.8, 10 mM KCl, 10 mM $(NH_4)_2SO_4$, 2 mM $MgSO_4$, 0.1% (v/v) Triton X100 and 0.1 mg/ml bovine serum albumin. Each reaction contained 250 μM each dATP, dGTP and dCTP. Reactions 1-4 contained 250 μM TTP; reactions 5-8 250 μM dUTP. 2.5 units of the polymerase were used. Cycle 1×10 minutes 94° C.; 30×1 minute 94° C./2 minutes 42° C./1 minute 72° C.; 1×10 minutes 72° C. The Pfu-Pol mutants V93Q and V93R give higher yield of PCR product (lanes 3,4) than wild type Pfu-Pol (lane 2) when TTP is used. Wild type Pfu-Pol does not give a PCR product with dUTP (lane 6), whereas Pfu-Pol mutants V93Q and V93R give a product (lanes 7,8) [lane 1=Taq-Pol with TTP; lane 2=Wild type Pfu-pol with TTP; lane 3=Pfu-Pol V93Q with TTP; lane 4=Pfu-Pol V93R with TTP; lane 5=Taq-Pol with dUTP; lane 6=Wild type Pfu-pol with dUTP; lane 7=Pfu-Pol V93Q with dUTP; lane 8=Pfu-Pol V93R with dUTP] [M=100 bp ladder; Mb=1 Kb ladder].

EXAMPLE 1

Crystal structures are known for five family B DNA polymerases; one viral, the remaining four archaeal. The first structure to be solved was for the bacteriophage RB69 polymerase (RB69-Pol) (J. Wang et al., *Cell* 89, 1087 (1997)); a structure with primer-template has also been determined (M. C. Franklin, J. J. Wang, T. A. Steitz, *Cell* 105, 657 (2001)).

More recently, the structure of an archaeal family B DNA polymerase. from the hyperthermophilic archaeon *Thermococcus gorgonarius* (Tgo-Pol), has been reported (K. P. Hopfner et al., Structure 7, 1189 PNAS 96, 3600 (1999)). Three other archaeal polymerase structures, *Desulfurococcus* strain Tok (DTok-Pol) (Y. Zhao et al., Structure 7, 1189 (1999)). Three other archaeal polymerase structures, *Desulfurococcus* strain Tok (DTok-Pol) (Y. Zhao et al, *Structure* 7, 1189 (1999)), *Thermococcus* sp. 9° N-7 (9° N-7-Pol) (A. C. Rodgriguez, H-W. Park, C. Mao, L. S. Beene, *J. Mol. Biol.* 299, 447 (200)) and *Pyrococcus kodakaraensis* KOD1 (KOD1-Pol) (H. Hashimoto et al., *J. Mol. Biol.* 306, 469 (2001)), were subsequently solved. Only apo-enzyme structures are known for the archaea. All five family B polymerases contain five distinct domains, the N-terminal domain, the exonuclease or 'editing' domain and three polymerase active site domains. The folding of the five domains forms three distinct clefts extending from a central hole. Two (named clefts D and T) are oriented approximately 180° relative to each other, on either side of the central hole. The structure of RB69-pol containing a primer-template demonstrates that cleft D binds double stranded primer-template and cleft T binds single-stranded template (M. C. Franklin el al supra). The three polymerase domains forms cleft D, whereas cleft T is formed by the exonuclease domain and the N-terminal domain. The third cleft is perpendicular to the other two and represents the 3'-5' exonucleaseiediting cleft.

Examination of cleft T in the case of Tgo-Pol (the other archaeal polymerases give similar results) revealed the presence of a pocket located on a surface exposed face towards the outer edge of the polymerase (FIG. 2A). The location of this pocket, in the template strand binding region, approximately four bases from the primer-template junction makes it a clear candidate for uracil recognition. The pocket is comprised of amino acids that are solely present in the N-terminal domain. Amino acids from four regions of this domain, which are close together in space, are used to assemble the putative uracil binding pocket. These amino acids are illustrated in FIG. 2B (a structural representation of the N-terminal domain) and underlined in FIG. 2C (the amino acid sequence of the N-terminal domain). The function of Y7, which sits at the entrance of the pocket, is obscure. It may form a lid, which closes following binding, ensuring trapping (and hence high affinity) of uracil. The base of the pocket (clearly visible as P36/Y37 in FIG. 2B) is formed by Y37 and by P36 at the beginning of a β sheet and supported by K84 "underneath" Y37. One side of the pocket is formed by amino acids 90-97, present in a α-helix. A proline (P94) bends the α-helix, forming a curved wall (FIG. 2B). The other side comprises residues 110-116; amino acids present in a loop region (110-114) or at the beginning of a second α-helix (115-116). This α-helix commences with amino acids P115 and F116. The proline appears to have a critical role, ensuring that P115 and F116 are able to form part of the pocket's curved wall (FIG. 2B).

The viral polymerase from RB-69 shows 61% amino acid identity to bacteriophage T4-Pol. Additionally, the N-terminal of RB69-Pol is identical to a structure for an N-terminal fragment of T4-Pol (J. Wang, P. Yu, T. C. Lin, W. H. Konigsberg, T. A. Steitz, *Biochemistry* 35, 8110 (1996)). Previously, it has been demonstrated that T4-Pol did not stall polymerisation in response to template-strand uracil (M. A. Greagg et al., *Proc Natl. Acad. Sci. USA.* 96, (1999)); inability to recognize uracil would also be expected for RB69-Pol. This contrasts with Tgo-Pol which stalls polymerization when template strand uracil is encountered (M. A. Greagg et al., Supra). Tgo-Pol is also inhibited by uracil containing DNA (R. S. Lasken, D. M. Schuster, A. Rashtchian, *J. Biol. Chem.* 271, 17692 (1996)); a feature not seen with viral enzymes.

Therefore, if the pocket seen with Tgo-Pol is used for uracil detection, it should be absent for the viral enzymes. The N-terminal domains of Tgo-Pol and RB69-Pol show considerable structural homology (FIG. 2D); near perfect alignment of secondary structural elements is observed, despite the almost complete lack of amino acid sequence homology (FIG. 2C). The only significant difference is the presence of an amino acid insert (shown in FIG. 2D) in the archaeal enzyme. However, detailed comparisons demonstrate differences in the two polymerases (FIG. 2E). With Tgo-Pol, Y7 may act as a lid and Y36 forms the base of the pocket; in RB-69 these residues are replaced with valine/glutamine (both these amino acids in RB69-Pol are near Y7 of Tgo-Pol and it is not clear which is the exact replacement) and serine respectively. Similarly Tgo-Pol uses a proline-containing kinked α-helix (residues 90-97) to form one wall of the pocket. In RB69-Pol the corresponding α-helix (residues 65-74) lacks the proline; therefore, the helix is straight and does not form a good wall. However, a key feature involves P115 and F116, which form part of one of the walls of the pocket with Tgo-Pol. In the case of RB69 the proline is missing and this results in the corresponding phenylalanine (F88) falling into and completely filling the pocket. As shown in FIG. 1E this means that the viral enzyme lacks a uracil binding pocket (P35/S36 are substantially obscured). The differences between the viral and archaeal enzymes, based on subtle changes to a few amino acids, provide compelling evidence that the N-terminal pocket is responsible for uracil detection.

It was possible to model uracil into the pocket of Tgo-Pol (FIG. 3A). The most favourable orientation produces four hydrogen bonds between the protein and uracil. In all cases the protein uses the peptide backbone for hydrogen bond formation. The interactions comprise: I114 (peptide —NH) to uracil C2 $=$O group; E111 (peptide $=$O) to uracil N3H; Y37 (peptide $=$O) to uracil N3H and (peptide —NH) to uracil C4$=$0 (FIG. 3A). Cytosine superimposed at the same position as uracil forms only one hydrogen bond (I114 (peptide —NH) to uracil C2 $=$O) and the 4-$NH_2$ group clashes with the main chain atoms of Y37 (peptide $=$O and —NH) (FIG. 3B). This clash could be relieved by repositioning the cytosine, but only at the expense of the one H-bond, resulting in no interactions between the base and the protein. Thymine superimposed at the uracil position could form most of the protein-base hydrogen bonds (interactions were identical to uracil except the Y37 (peptide —NH) to uracil/thymine N3H hydrogen bond was not formed). Critically the C5 —$CH_3$ group showed a severe steric clash with the edges of the cyclic P36 side chain and the ring of F116, thereby preventing binding of the base within the pocket (FIG. 3C). Thus the pocket is highly specific for binding uracil and able to discriminate against the 'normal' DNA pyrimidines.

An amino acid sequence alignment has been carried out for the N-terminal domains of fourteen archaeal family B DNA polymerases (FIG. 1); eight were from the crenarchaea and six from the euryarchaea. Twelve of the polymerases were either thermophiles or hyperthermophiles, one was mesophilic (*Methanococcus voltae* (Mvo)) and one was psychrophilic (*Cenarchaeaum symbiosum* (Csy)). Two highly conserved regions (A and B) which contain most of the amino acids that from the uracil binding pocket, are seen. Many of the amino acids comprising the uracil binding pocket (FIGS. 2B and 2C) are highly conserved; especially uracil-contacting residues (FIG. 3A). Thus P36, Y37, E111 and I114 show 100% identity. The possible pocket lid, Y7, also shows 100% conservation. Several other key amino acids e.g. V93 (which lines one side of the pocket), P115 and F116 (which line the other side of the pocket) show a high degree of conservation.

EXAMPLE 2

Use was made of three assays to test the ability of the mutant polymerases to recognise uracil. Primer extension reactions (M. A. Greagg et al., Supra) measure the ability of a polymerase to extend a primer through uracil bases in the template strand. As expected both the wild type and the mutant enzymes were able to completely copy a control template, lacking uracil (FIG. 4A). As previously observed (M. A. Greagg et al., Supra), the wild type enzyme stalled polymerisation four bases upstream of template-strand uracil, resulting in a truncated product (FIG. 4B). Y37A, Y37F and P115F behaved in a similar manner to wild type. However, three of the mutant enzymes, V93Q, P115Δ and Y7A, produced full-length product when uracil was present (FIG. 4B). With V93Q full-length product predominated; in the cases of P115Δ and Y7A both full-length and truncated product were seen.

Next the ability of the polymerases to bind single stranded DNA containing uracil was investigated, using a binding assay based on fluorescence anisotropy (S. L. Reid, D. Parry, H-H. Liu, B. A. Connolly, *Biochemistry* 40, 2484 (2001)). $K_D$ was determined by fluorescence anisotropy used an oligodeoxynucleotide containing a single uracil and a hexachlorofluorescein label at its 5′-terminal. The oligodeoxynucleotide used was: 5′-hex-GCCCGCGGGAUATCGGCCCTTA-3′ (SEQ ID NO.16) (or a control in which the uracil was replaced with thymine). The concentration of the oligodeoxynucleotide was 5 nM in 1 ml of 10 mM Hepes-NaOH, pH7.5, 100 mM NaCl, 1 mM EDTA. Aliquots of the enzyme were added and the anisotropy measured; titration was continued until the anisotropy stopped increasing. Data fitting to obtain $K_D$ values is as described by Reid et al (Supra)). $K_D$ values are summarised in table 1. The wild type enzyme bound the uracil-containing oligodeoxynucleotide with a $K_D$ of 8.3 nM, a 17-fold preference over a control strand lacking this base. Three of the mutants, Y7A, V93Q and P115Δ bound to the uracil-containing oligodeoxynucleotide less well than the wild type ($K_D$ values of 25.7, 144.5 and 84 nM respectively, table 1). These mutants correspond exactly to those able to read through a uracil-containing template; furthermore the diminution in uracil binding corresponds with read through capability. In both assays loss of uracil recognition is: V93Q>P115Δ>Y7A. These three mutants also show a reduced preference for uracil-containing DNA over the control sequence; with P115Δ and V93Q the preference is virtually abolished. The mutants Y7A, Y37A and P115F bind uracil-containing DNA with essentially the same affinity as the wild type (table 1). In some cases, Y37A and Y37F, the preference for the uracil-containing oligodeoxynucleotide is reduced, but this arises solely from tighter binding of the control. Table 1 also gives the specific activity of the mutant Pfu-Pols relative to the wild type. In general there are only small decreases in activity with even the mutant with the lowest activity (Y7A) retaining 38% of the wild type activity.

The DNA polymerase activity assay (Richardson, C. C. (1966) in Procedures in *Nucleic Acids Research*, G. L. Cantoni, D. R. Davies, Eds, (Harper and Row, New York, 1966), pp. 263-27) used 50 μl samples containing 20 mM Tris-HCl, pH 8.8, 10 mM KCl, 10 mM (NH$_4$)$_2$SO$_4$, 2 mM MgSO$_4$, 0.1% Triton X100, 100 μg/ml BSA, 200 μM each dNTPs, 0.2 mg/ml activated calf thymus DNA (AP Biotech), 1 μCi 3000 Ci/mmol [α-$^{32}$P] dATP. Pfu-Pol (the amount varied depending on the activity of the enzyme) was added and a 10 minute incubation at 72° C. was used (reactions were linear over this time). After this period the amount of radioactivity incorporated into acid-precipitable material was determined by scintillation counting. 1 unit of enzyme is defined as amount of enzyme that incorporates 10 nmol of dATP into acid-precipitable material in 30 min at 72° C.

TABLE 1

Pfu-Pol variants: specific activity and ability to bind to uracil containing DNA.

| Pfu-Pol variant | specific activity (units/mg) | % activity (relative to wild type) | $K_D$ (nM) (uracil) | $K_D$ (nM) (control) | Preference for uracil |
|---|---|---|---|---|---|
| wild-type | 3556 | 100 | 8 ± 1 | 140 ± 10 | 18 |
| Y7A | 2314 | 65 | 26 ± 1 | 255 ± 20 | 10 |
| Y37A | 1352 | 38 | 9 ± 2 | 57 ± 7 | 6 |
| Y37F | 2169 | 61 | 10 ± 4 | 120 ± 13 | 12 |
| V93Q | 1643 | 46 | 144 ± 7 | 277 ± 22 | 2 |
| P115F | 2541 | 71 | 7 ± 1 | 148 ± 10 | 21 |
| P115Δ | 1637 | 46 | 84 ± 4 | 111 ± 5 | 1.3 |

The specific activities of the Pfu-Pol variants was determined using the incorporation of [α-$^{32}$P]-dATP into acid-precipitable calf-thymus DNA as described (see above). Values are accurate ±15%. Binding constants were determined by fluorescence anisotropy using hex-GCCCGCGG-GAUATCGGCCCTTA (SEQ ID NO.16) (uracil) or an analogous oligodeoxynucleotide in which the uracil was replaced with thymine (control) (S. L. Reid, et al; supra and J. Wang et al., (Supra)). Each value was determined three times and the average ±one standard deviation is given. The preference for uracil is the ratio $K_{D\ (uracil)}/K_{D\ (control)}$.

Finally PCR was performed +/− dUTP the ability of Pfu-Pol to carry out PCR was evaluated by amplifying a −2 kbase fragment (between the T7 promoter and the HindIII site) of pET17-b(Pfu-Pol) [S. J. Evans et al., *Nucl. Acids. Res.* 28, 1059 (2000)]. Conditions: 100 μl volume, 20 mM Tris-HCl ph 8.8, 10 mM KCl, 10 mM (NH$_4$)$_2$SO$_4$, 0.1% Triton X100, 100 μg/ml BSA, 250 μM each dNTP (one set of reactions contained dTTP, the other dUTP), 2.5 units DNA polymerase overlayed with 40 μl of mineral oil. 5 ng of pET17-b(Pfu-Pol) was used and the concentrations of the forward and reverse primers were both 0.3 μM. Each reaction was 30 cycles of 1 min at 95° C., 2 min at 52° C. and 4.5 min at 72° C. PCR with Taq-Pol was identical to Pfu-Pol save 10 mM Tris-HCl pH 8.8, 50 mM KCl, 0.08% NP-40, 1.5 mM MgCl$_2$ was used. Analysis used ethidium bromide-stained agarose gels.

Pfu-Pol (wild type and mutants) and Taq-Pol, were able to perform PCR with the four normal dNTPs (FIG. 4C). When dUTP was used in place of dTTP, PCR with Taq-Pol was unaffected; however, wild-type Pfu-Pol gave no product (FIG. 4D). The three mutants that showed diminished uracil recognition in read-through and binding assays, Y7A, P115Δ and V93Q, gave a PCR product (FIG. 4D). The amount of PCR product produced was V93Q>P115Δ>Y7A, again matching the order found for loss of uracil recognition. dUTP (concentration 250 μM) completely replaces dTTP in these reactions. The wild type enzyme is completely inhibited when 0.02 μM dUTP is used to spike PCR reactions containing the four normal dNTPs (H. H. Hogrefe, et al (Supra)); clearly showing these three mutants are very disabled in uracil recognition. The Pfu-Pol mutants, Y37A, Y37F and P115F did not give a PCR product with dUTP.

FIG. 5 shows the results of PCR with *Thermus aquaticus* polymerase (Taq-Pol), the wild type and two mutants (V93Q and V93R) of *Pyrococcus furiosus* polymerase (Pfu-Pol). PCR amplification was performed under two distinct sets of conditions, i.e. in the presence of TTP and in the presence of dUTP.

As expected, all four polymerases, Taq-Pol, the wild type of Pfu-pol and the two mutations of Pfu-pol (V93Q, V93R), were able to successfully mediate amplification of the DNA sample in the presence of TTP. Clearly visible bands of 1064 bp fragments in lanes 1 to 4 illustrate this successful amplification. The use of dUTP resulted in the expected amount of amplification when used together with Taq-Pol as illustrated in lane 5. Moreover, lane 6 shows no amplified DNA sample and thereby confirmed that dUTP induces blockage of Pfu-Pol mediated amplification. Most importantly, however, lanes 7 and 8 show bands corresponding to 1064 bp fragments and thus confirm that both Pfu polymerase mutants are capable of amplification. This proves that, unlike wild type Pfu-Pol, the V93Q and V93R mutants of Pfu-Pol are not affected by dUTP-induced blockage.

Overall, FIG. 5 confirms the usefulness of the mutants according to the invention in PCR utilizing dUTP.

The invention claimed is:

1. A variant archaeal family B DNA polymerase comprising the amino acid sequence of SEQ ID NO:2 with a substitution at position V93, the substitution being in the amino-terminal amino acids that comprise a uracil-binding pocket in a wild-type family B DNA polymerase amino acid sequence whereby the variant polymerase has reduced affinity for uracil as compared to the wild-type polymerase.

2. The variant archaeal family B DNA polymerase according to claim 1 wherein the wildtype family B DNA polymerase is *Pyrococcus furiosus* DNA polymerase (Pfu-Pol).

3. The variant archaeal DNA polymerase according to claim 1 wherein the substitution is V93Q.

4. The variant archaeal DNA polymerase according to claim 1 wherein the substitution is V93R.

5. A kit useful for polymerase chain reactions comprising a variant archaeal family B DNA polymerase as defined in claim 1.

6. The kit of claim 5, further comprising DNA to be amplified, free bases, primers and combinations thereof.

* * * * *

SEQUENCE LISTING

```
<160> NUMBER OF SEQ ID NOS: 33

<210> SEQ ID NO 1
<211> LENGTH: 776
<212> TYPE: PRT
<213> ORGANISM: Unknown
<220> FEATURE:
<223> OTHER INFORMATION: Variant derived from Pyrococcus furiosus
      Pfu-Polymerase

<400> SEQUENCE: 1

Met Ala Ile Leu Asp Val Asp Tyr Ile Thr Glu Glu Gly Lys Pro Val
1               5                   10                  15

Ile Arg Leu Phe Lys Lys Glu Asn Gly Lys Phe Lys Ile Glu His Asp
            20                  25                  30

Arg Thr Phe Arg Pro Tyr Ile Tyr Ala Leu Leu Arg Asp Asp Ser Lys
        35                  40                  45

Ile Glu Glu Val Lys Lys Ile Thr Gly Glu Arg His Gly Lys Ile Val
    50                  55                  60

Arg Ile Val Asp Val Glu Lys Val Glu Lys Lys Phe Leu Gly Lys Pro
65                  70                  75                  80

Ile Thr Val Trp Lys Leu Tyr Leu Glu His Pro Gln Asp Val Pro Thr
                85                  90                  95

Ile Arg Glu Lys Val Arg Glu His Pro Ala Val Val Asp Ile Phe Glu
            100                 105                 110

Tyr Asp Ile Pro Phe Ala Lys Arg Tyr Leu Ile Asp Lys Gly Leu Ile
        115                 120                 125

Pro Met Glu Gly Glu Glu Leu Lys Ile Leu Ala Phe Asp Ile Glu
    130                 135                 140

Thr Leu Tyr His Glu Gly Glu Glu Phe Gly Lys Gly Pro Ile Ile Met
145                 150                 155                 160

Ile Ser Tyr Ala Asp Glu Asn Glu Ala Lys Val Ile Thr Trp Lys Asn
                165                 170                 175

Ile Asp Leu Pro Tyr Val Glu Val Val Ser Ser Glu Arg Glu Met Ile
            180                 185                 190

Lys Arg Phe Leu Arg Ile Ile Arg Glu Lys Asp Pro Asp Ile Ile Val
        195                 200                 205

Thr Tyr Asn Gly Asp Ser Phe Asp Phe Pro Tyr Leu Ala Lys Arg Ala
    210                 215                 220

Glu Lys Leu Gly Ile Lys Leu Thr Ile Gly Arg Asp Gly Ser Glu Pro
225                 230                 235                 240

Lys Met Gln Arg Ile Gly Asp Met Thr Ala Val Glu Val Lys Gly Arg
                245                 250                 255

Ile His Phe Asp Leu Tyr His Val Ile Thr Arg Thr Ile Asn Leu Pro
            260                 265                 270
```

```
Thr Tyr Thr Leu Glu Ala Val Tyr Glu Ala Ile Phe Gly Lys Pro Lys
        275                 280                 285

Glu Lys Val Tyr Ala Asp Glu Ile Ala Lys Ala Trp Glu Ser Gly Glu
    290                 295                 300

Asn Leu Glu Arg Val Ala Lys Tyr Ser Met Glu Asp Ala Lys Ala Thr
305                 310                 315                 320

Tyr Glu Leu Gly Lys Glu Phe Leu Pro Met Glu Ile Gln Leu Ser Arg
                325                 330                 335

Leu Val Gly Gln Pro Leu Trp Asp Val Ser Arg Ser Ser Thr Gly Asn
                340                 345                 350

Leu Val Glu Trp Phe Leu Leu Arg Lys Ala Tyr Glu Arg Asn Glu Val
                355                 360                 365

Ala Pro Asn Lys Pro Ser Glu Glu Tyr Gln Arg Arg Leu Arg Glu
370                 375                 380

Ser Tyr Thr Gly Gly Phe Val Lys Glu Pro Glu Lys Gly Leu Trp Glu
385                 390                 395                 400

Asn Ile Val Tyr Leu Asp Phe Arg Ala Leu Tyr Pro Ser Ile Ile Ile
                405                 410                 415

Thr His Asn Val Ser Pro Asp Thr Leu Asn Leu Glu Gly Cys Lys Asn
                420                 425                 430

Tyr Asp Ile Ala Pro Gln Val Gly His Lys Phe Cys Lys Asp Ile Pro
                435                 440                 445

Gly Phe Ile Pro Ser Leu Leu Gly His Leu Leu Glu Glu Arg Gln Lys
                450                 455                 460

Ile Lys Thr Lys Met Lys Glu Thr Gln Asp Pro Ile Glu Lys Ile Leu
465                 470                 475                 480

Leu Asp Tyr Arg Gln Lys Ala Ile Lys Leu Leu Ala Asn Ser Phe Tyr
                485                 490                 495

Gly Tyr Tyr Gly Tyr Ala Lys Ala Arg Trp Tyr Cys Lys Glu Cys Ala
                500                 505                 510

Glu Ser Val Thr Ala Trp Gly Arg Lys Tyr Ile Glu Leu Val Trp Lys
                515                 520                 525

Glu Leu Glu Glu Lys Phe Gly Phe Lys Val Leu Tyr Ile Asp Thr Asp
                530                 535                 540

Gly Leu Tyr Ala Thr Ile Pro Gly Gly Glu Ser Glu Glu Ile Lys Lys
545                 550                 555                 560

Lys Ala Leu Glu Phe Val Lys Tyr Ile Asn Ser Lys Leu Pro Gly Leu
                565                 570                 575

Leu Glu Leu Glu Tyr Glu Gly Phe Tyr Lys Arg Gly Phe Phe Val Thr
                580                 585                 590

Lys Lys Arg Tyr Ala Val Ile Asp Glu Glu Gly Lys Val Ile Thr Arg
                595                 600                 605

Gly Leu Glu Ile Val Arg Arg Asp Trp Ser Glu Ile Ala Lys Glu Thr
610                 615                 620

Gln Ala Arg Val Leu Glu Thr Ile Leu Lys His Gly Asp Val Glu Glu
625                 630                 635                 640

Ala Val Arg Ile Val Lys Glu Val Ile Gln Lys Leu Ala Asn Tyr Glu
                645                 650                 655

Ile Pro Pro Glu Lys Leu Ala Ile Tyr Glu Gln Ile Thr Arg Pro Leu
                660                 665                 670

His Glu Tyr Lys Ala Ile Gly Pro His Val Ala Val Ala Lys Lys Leu
                675                 680                 685

Ala Ala Lys Gly Val Lys Ile Lys Pro Gly Met Val Ile Gly Tyr Ile
690                 695                 700
```

-continued

Val Leu Arg Gly Asp Gly Pro Ile Ser Asn Arg Ala Ile Leu Ala Glu
705                 710                 715                 720

Glu Tyr Asp Pro Lys Lys His Lys Tyr Asp Ala Glu Tyr Tyr Ile Glu
            725                 730                 735

Asn Gln Val Leu Pro Ala Val Leu Arg Ile Leu Glu Gly Phe Gly Tyr
        740                 745                 750

Arg Lys Glu Asp Leu Arg Tyr Gln Lys Thr Arg Gln Val Gly Leu Thr
    755                 760                 765

Ser Trp Leu Asn Ile Lys Lys Ser
770                 775

<210> SEQ ID NO 2
<211> LENGTH: 775
<212> TYPE: PRT
<213> ORGANISM: Pyrococcus furiosus

<400> SEQUENCE: 2

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

-continued

```
Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
            325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
        370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
```

```
                       725                 730                 735
Gln Val Leu Pro Ala Val Leu Arg Ile Leu Glu Gly Phe Gly Tyr Arg
                   740                 745                 750

Lys Glu Asp Leu Arg Tyr Gln Lys Thr Arg Gln Val Gly Leu Thr Ser
               755                 760                 765

Trp Leu Asn Ile Lys Lys Ser
           770                 775

<210> SEQ ID NO 3
<211> LENGTH: 776
<212> TYPE: PRT
<213> ORGANISM: Unknown
<220> FEATURE:
<223> OTHER INFORMATION: Variant derived from Pyrococcus furiosus
      Pfu-Polymerase

<400> SEQUENCE: 3

Met Ala Ile Leu Asp Val Asp Ala Ile Thr Glu Glu Gly Lys Pro Val
1               5                   10                  15

Ile Arg Leu Phe Lys Lys Glu Asn Gly Lys Phe Lys Ile Glu His Asp
            20                  25                  30

Arg Thr Phe Arg Pro Tyr Ile Tyr Ala Leu Leu Arg Asp Asp Ser Lys
        35                  40                  45

Ile Glu Glu Val Lys Lys Ile Thr Gly Glu Arg His Gly Lys Ile Val
50                  55                  60

Arg Ile Val Asp Val Glu Lys Val Glu Lys Phe Leu Gly Lys Pro
65                  70                  75                  80

Ile Thr Val Trp Lys Leu Tyr Leu Glu His Pro Gln Asp Val Pro Thr
            85                  90                  95

Ile Arg Glu Lys Val Arg Glu His Pro Ala Val Val Asp Ile Phe Glu
        100                 105                 110

Tyr Asp Ile Pro Phe Ala Lys Arg Tyr Leu Ile Asp Lys Gly Leu Ile
    115                 120                 125

Pro Met Glu Gly Glu Glu Leu Lys Ile Leu Ala Phe Asp Ile Glu
130                 135                 140

Thr Leu Tyr His Glu Gly Glu Glu Phe Gly Lys Gly Pro Ile Ile Met
145                 150                 155                 160

Ile Ser Tyr Ala Asp Glu Asn Glu Ala Lys Val Ile Thr Trp Lys Asn
                165                 170                 175

Ile Asp Leu Pro Tyr Val Glu Val Val Ser Ser Glu Arg Glu Met Ile
            180                 185                 190

Lys Arg Phe Leu Arg Ile Ile Arg Glu Lys Asp Pro Asp Ile Ile Val
        195                 200                 205

Thr Tyr Asn Gly Asp Ser Phe Asp Phe Pro Tyr Leu Ala Lys Arg Ala
    210                 215                 220

Glu Lys Leu Gly Ile Lys Leu Thr Ile Gly Arg Asp Gly Ser Glu Pro
225                 230                 235                 240

Lys Met Gln Arg Ile Gly Asp Met Thr Ala Val Glu Val Lys Gly Arg
                245                 250                 255

Ile His Phe Asp Leu Tyr His Val Ile Thr Arg Thr Ile Asn Leu Pro
            260                 265                 270

Thr Tyr Thr Leu Glu Ala Val Tyr Glu Ala Ile Phe Gly Lys Pro Lys
        275                 280                 285

Glu Lys Val Tyr Ala Asp Glu Ile Ala Lys Ala Trp Glu Ser Gly Glu
    290                 295                 300

Asn Leu Glu Arg Val Ala Lys Tyr Ser Met Glu Asp Ala Lys Ala Thr
```

```
            305                 310                 315                 320
Tyr Glu Leu Gly Lys Glu Phe Leu Pro Met Glu Ile Gln Leu Ser Arg
                    325                 330                 335

Leu Val Gly Gln Pro Leu Trp Asp Val Ser Arg Ser Thr Gly Asn
                340                 345                 350

Leu Val Glu Trp Phe Leu Leu Arg Lys Ala Tyr Glu Arg Asn Glu Val
                355                 360                 365

Ala Pro Asn Lys Pro Ser Glu Glu Tyr Gln Arg Arg Leu Arg Glu
            370                 375                 380

Ser Tyr Thr Gly Gly Phe Val Lys Glu Pro Glu Lys Gly Leu Trp Glu
385                 390                 395                 400

Asn Ile Val Tyr Leu Asp Phe Arg Ala Leu Tyr Pro Ser Ile Ile Ile
                405                 410                 415

Thr His Asn Val Ser Pro Asp Thr Leu Asn Leu Glu Gly Cys Lys Asn
                420                 425                 430

Tyr Asp Ile Ala Pro Gln Val Gly His Lys Phe Cys Lys Asp Ile Pro
                435                 440                 445

Gly Phe Ile Pro Ser Leu Leu Gly His Leu Leu Glu Glu Arg Gln Lys
            450                 455                 460

Ile Lys Thr Lys Met Lys Glu Thr Gln Asp Pro Ile Glu Lys Ile Leu
465                 470                 475                 480

Leu Asp Tyr Arg Gln Lys Ala Ile Lys Leu Leu Ala Asn Ser Phe Tyr
                    485                 490                 495

Gly Tyr Tyr Gly Tyr Ala Lys Ala Arg Trp Tyr Cys Lys Glu Cys Ala
                500                 505                 510

Glu Ser Val Thr Ala Trp Gly Arg Lys Tyr Ile Glu Leu Val Trp Lys
            515                 520                 525

Glu Leu Glu Glu Lys Phe Gly Phe Lys Val Leu Tyr Ile Asp Thr Asp
            530                 535                 540

Gly Leu Tyr Ala Thr Ile Pro Gly Gly Glu Ser Glu Glu Ile Lys Lys
545                 550                 555                 560

Lys Ala Leu Glu Phe Val Lys Tyr Ile Asn Ser Lys Leu Pro Gly Leu
                565                 570                 575

Leu Glu Leu Glu Tyr Glu Gly Phe Tyr Lys Arg Gly Phe Phe Val Thr
                580                 585                 590

Lys Lys Arg Tyr Ala Val Ile Asp Glu Glu Gly Lys Val Ile Thr Arg
            595                 600                 605

Gly Leu Glu Ile Val Arg Arg Asp Trp Ser Glu Ile Ala Lys Glu Thr
610                 615                 620

Gln Ala Arg Val Leu Glu Thr Ile Leu Lys His Gly Asp Val Glu Glu
625                 630                 635                 640

Ala Val Arg Ile Val Lys Glu Val Ile Gln Lys Leu Ala Asn Tyr Glu
                645                 650                 655

Ile Pro Pro Glu Lys Leu Ala Ile Tyr Glu Gln Ile Thr Arg Pro Leu
                660                 665                 670

His Glu Tyr Lys Ala Ile Gly Pro His Val Ala Val Ala Lys Lys Leu
            675                 680                 685

Ala Ala Lys Gly Val Lys Ile Lys Pro Gly Met Val Ile Gly Tyr Ile
            690                 695                 700

Val Leu Arg Gly Asp Gly Pro Ile Ser Asn Arg Ala Ile Leu Ala Glu
705                 710                 715                 720

Glu Tyr Asp Pro Lys Lys His Lys Tyr Asp Ala Glu Tyr Tyr Ile Glu
                725                 730                 735
```

```
Asn Gln Val Leu Pro Ala Val Leu Arg Ile Leu Glu Gly Phe Gly Tyr
            740                 745                 750
Arg Lys Glu Asp Leu Arg Tyr Gln Lys Thr Arg Gln Val Gly Leu Thr
        755                 760                 765
Ser Trp Leu Asn Ile Lys Lys Ser
    770                 775

<210> SEQ ID NO 4
<211> LENGTH: 776
<212> TYPE: PRT
<213> ORGANISM: Unknown
<220> FEATURE:
<223> OTHER INFORMATION: Variant derived from Pyrococcus furiosus
      Pfu-Polymerase

<400> SEQUENCE: 4

Met Ala Ile Leu Asp Val Asp Tyr Ile Thr Glu Glu Gly Lys Pro Val
1               5                   10                  15
Ile Arg Leu Phe Lys Lys Glu Asn Gly Lys Phe Lys Ile Glu His Asp
            20                  25                  30
Arg Thr Phe Arg Pro Ala Ile Tyr Ala Leu Leu Arg Asp Asp Ser Lys
        35                  40                  45
Ile Glu Glu Val Lys Lys Ile Thr Gly Glu Arg His Gly Lys Ile Val
    50                  55                  60
Arg Ile Val Asp Val Glu Lys Val Glu Lys Lys Phe Leu Gly Lys Pro
65                  70                  75                  80
Ile Thr Val Trp Lys Leu Tyr Leu Glu His Pro Gln Asp Val Pro Thr
                85                  90                  95
Ile Arg Glu Lys Val Arg Glu His Pro Ala Val Val Asp Ile Phe Glu
            100                 105                 110
Tyr Asp Ile Pro Phe Ala Lys Arg Tyr Leu Ile Asp Lys Gly Leu Ile
        115                 120                 125
Pro Met Glu Gly Glu Glu Glu Leu Lys Ile Leu Ala Phe Asp Ile Glu
    130                 135                 140
Thr Leu Tyr His Glu Gly Glu Glu Phe Gly Lys Gly Pro Ile Ile Met
145                 150                 155                 160
Ile Ser Tyr Ala Asp Glu Asn Glu Ala Lys Val Ile Thr Trp Lys Asn
                165                 170                 175
Ile Asp Leu Pro Tyr Val Glu Val Val Ser Ser Glu Arg Glu Met Ile
            180                 185                 190
Lys Arg Phe Leu Arg Ile Ile Arg Glu Lys Asp Pro Asp Ile Ile Val
        195                 200                 205
Thr Tyr Asn Gly Asp Ser Phe Asp Phe Pro Tyr Leu Ala Lys Arg Ala
    210                 215                 220
Glu Lys Leu Gly Ile Lys Leu Thr Ile Gly Arg Asp Gly Ser Glu Pro
225                 230                 235                 240
Lys Met Gln Arg Ile Gly Asp Met Thr Ala Val Glu Val Lys Gly Arg
                245                 250                 255
Ile His Phe Asp Leu Tyr His Val Ile Thr Arg Thr Ile Asn Leu Pro
            260                 265                 270
Thr Tyr Thr Leu Glu Ala Val Tyr Glu Ala Ile Phe Gly Lys Pro Lys
        275                 280                 285
Glu Lys Val Tyr Ala Asp Glu Ile Ala Lys Ala Trp Glu Ser Gly Glu
    290                 295                 300
Asn Leu Glu Arg Val Ala Lys Tyr Ser Met Glu Asp Ala Lys Ala Thr
305                 310                 315                 320
```

-continued

```
Tyr Glu Leu Gly Lys Glu Phe Leu Pro Met Glu Ile Gln Leu Ser Arg
            325                 330                 335

Leu Val Gly Gln Pro Leu Trp Asp Val Ser Arg Ser Ser Thr Gly Asn
        340                 345                 350

Leu Val Glu Trp Phe Leu Leu Arg Lys Ala Tyr Glu Arg Asn Glu Val
        355                 360                 365

Ala Pro Asn Lys Pro Ser Glu Glu Tyr Gln Arg Arg Leu Arg Glu
370                 375                 380

Ser Tyr Thr Gly Gly Phe Val Lys Glu Pro Glu Lys Gly Leu Trp Glu
385                 390                 395                 400

Asn Ile Val Tyr Leu Asp Phe Arg Ala Leu Tyr Pro Ser Ile Ile Ile
                405                 410                 415

Thr His Asn Val Ser Pro Asp Thr Leu Asn Leu Glu Gly Cys Lys Asn
            420                 425                 430

Tyr Asp Ile Ala Pro Gln Val Gly His Lys Phe Cys Lys Asp Ile Pro
        435                 440                 445

Gly Phe Ile Pro Ser Leu Leu Gly His Leu Leu Glu Glu Arg Gln Lys
450                 455                 460

Ile Lys Thr Lys Met Lys Glu Thr Gln Asp Pro Ile Glu Lys Ile Leu
465                 470                 475                 480

Leu Asp Tyr Arg Gln Lys Ala Ile Lys Leu Leu Ala Asn Ser Phe Tyr
                485                 490                 495

Gly Tyr Tyr Gly Tyr Ala Lys Ala Arg Trp Tyr Cys Lys Glu Cys Ala
            500                 505                 510

Glu Ser Val Thr Ala Trp Gly Arg Lys Tyr Ile Glu Leu Val Trp Lys
        515                 520                 525

Glu Leu Glu Glu Lys Phe Gly Phe Lys Val Leu Tyr Ile Asp Thr Asp
530                 535                 540

Gly Leu Tyr Ala Thr Ile Pro Gly Gly Glu Ser Glu Glu Ile Lys Lys
545                 550                 555                 560

Lys Ala Leu Glu Phe Val Lys Tyr Ile Asn Ser Lys Leu Pro Gly Leu
                565                 570                 575

Leu Glu Leu Glu Tyr Glu Gly Phe Tyr Lys Arg Gly Phe Phe Val Thr
            580                 585                 590

Lys Lys Arg Tyr Ala Val Ile Asp Glu Glu Gly Lys Val Ile Thr Arg
        595                 600                 605

Gly Leu Glu Ile Val Arg Arg Asp Trp Ser Glu Ile Ala Lys Glu Thr
610                 615                 620

Gln Ala Arg Val Leu Glu Thr Ile Leu Lys His Gly Asp Val Glu Glu
625                 630                 635                 640

Ala Val Arg Ile Val Lys Glu Val Ile Gln Lys Leu Ala Asn Tyr Glu
                645                 650                 655

Ile Pro Pro Glu Lys Leu Ala Ile Tyr Glu Gln Ile Thr Arg Pro Leu
            660                 665                 670

His Glu Tyr Lys Ala Ile Gly Pro His Val Ala Val Ala Lys Lys Leu
        675                 680                 685

Ala Ala Lys Gly Val Lys Ile Lys Pro Gly Met Val Ile Gly Tyr Ile
690                 695                 700

Val Leu Arg Gly Asp Gly Pro Ile Ser Asn Arg Ala Ile Leu Ala Glu
705                 710                 715                 720

Glu Tyr Asp Pro Lys Lys His Lys Tyr Asp Ala Glu Tyr Tyr Ile Glu
                725                 730                 735

Asn Gln Val Leu Pro Ala Val Leu Arg Ile Leu Glu Gly Phe Gly Tyr
            740                 745                 750
```

```
Arg Lys Glu Asp Leu Arg Tyr Gln Lys Thr Arg Gln Val Gly Leu Thr
            755                 760                 765
Ser Trp Leu Asn Ile Lys Lys Ser
        770                 775

<210> SEQ ID NO 5
<211> LENGTH: 776
<212> TYPE: PRT
<213> ORGANISM: Unknown
<220> FEATURE:
<223> OTHER INFORMATION: Variant derived from Pyrococcus furiosus
      Pfu-Polymerase

<400> SEQUENCE: 5

Met Ala Ile Leu Asp Val Asp Tyr Ile Thr Glu Glu Gly Lys Pro Val
1               5                   10                  15

Ile Arg Leu Phe Lys Lys Glu Asn Gly Lys Phe Lys Ile Glu His Asp
            20                  25                  30

Arg Thr Phe Arg Pro Tyr Ile Tyr Ala Leu Leu Arg Asp Asp Ser Lys
        35                  40                  45

Ile Glu Glu Val Lys Lys Ile Thr Gly Glu Arg His Gly Lys Ile Val
50                  55                  60

Arg Ile Val Asp Val Glu Lys Val Lys Lys Phe Leu Gly Lys Pro
65                  70                  75                  80

Ile Thr Val Trp Lys Leu Tyr Leu Glu His Pro Gln Asp Gln Pro Thr
            85                  90                  95

Ile Arg Glu Lys Val Arg Glu His Pro Ala Val Val Asp Ile Phe Glu
        100                 105                 110

Tyr Asp Ile Pro Phe Ala Lys Arg Tyr Leu Ile Asp Lys Gly Leu Ile
            115                 120                 125

Pro Met Glu Gly Glu Glu Leu Lys Ile Leu Ala Phe Asp Ile Glu
    130                 135                 140

Thr Leu Tyr His Glu Gly Glu Glu Phe Gly Lys Gly Pro Ile Ile Met
145                 150                 155                 160

Ile Ser Tyr Ala Asp Glu Asn Glu Ala Lys Val Ile Thr Trp Lys Asn
                165                 170                 175

Ile Asp Leu Pro Tyr Val Glu Val Val Ser Ser Glu Arg Glu Met Ile
            180                 185                 190

Lys Arg Phe Leu Arg Ile Ile Arg Glu Lys Asp Pro Asp Ile Ile Val
        195                 200                 205

Thr Tyr Asn Gly Asp Ser Phe Asp Phe Pro Tyr Leu Ala Lys Arg Ala
    210                 215                 220

Glu Lys Leu Gly Ile Lys Leu Thr Ile Gly Arg Asp Gly Ser Glu Pro
225                 230                 235                 240

Lys Met Gln Arg Ile Gly Asp Met Thr Ala Val Glu Val Lys Gly Arg
                245                 250                 255

Ile His Phe Asp Leu Tyr His Val Ile Thr Arg Thr Ile Asn Leu Pro
            260                 265                 270

Thr Tyr Thr Leu Glu Ala Val Tyr Glu Ala Ile Phe Gly Lys Pro Lys
        275                 280                 285

Glu Lys Val Tyr Ala Asp Glu Ile Ala Lys Ala Trp Glu Ser Gly Glu
    290                 295                 300

Asn Leu Glu Arg Val Ala Lys Tyr Ser Met Glu Asp Ala Lys Ala Thr
305                 310                 315                 320

Tyr Glu Leu Gly Lys Glu Phe Leu Pro Met Glu Ile Gln Leu Ser Arg
                325                 330                 335
```

```
Leu Val Gly Gln Pro Leu Trp Asp Val Ser Arg Ser Ser Thr Gly Asn
            340                 345                 350

Leu Val Glu Trp Phe Leu Leu Arg Lys Ala Tyr Glu Arg Asn Glu Val
            355                 360                 365

Ala Pro Asn Lys Pro Ser Glu Glu Tyr Gln Arg Arg Leu Arg Glu
370                 375                 380

Ser Tyr Thr Gly Gly Phe Val Lys Glu Pro Glu Lys Gly Leu Trp Glu
385                 390                 395                 400

Asn Ile Val Tyr Leu Asp Phe Arg Ala Leu Tyr Pro Ser Ile Ile Ile
                405                 410                 415

Thr His Asn Val Ser Pro Asp Thr Leu Asn Leu Glu Gly Cys Lys Asn
                420                 425                 430

Tyr Asp Ile Ala Pro Gln Val Gly His Lys Phe Cys Lys Asp Ile Pro
                435                 440                 445

Gly Phe Ile Pro Ser Leu Leu Gly His Leu Leu Glu Glu Arg Gln Lys
450                 455                 460

Ile Lys Thr Lys Met Lys Glu Thr Gln Asp Pro Ile Glu Lys Ile Leu
465                 470                 475                 480

Leu Asp Tyr Arg Gln Lys Ala Ile Lys Leu Leu Ala Asn Ser Phe Tyr
                485                 490                 495

Gly Tyr Tyr Gly Tyr Ala Lys Ala Arg Trp Tyr Cys Lys Glu Cys Ala
                500                 505                 510

Glu Ser Val Thr Ala Trp Gly Arg Lys Tyr Ile Glu Leu Val Trp Lys
                515                 520                 525

Glu Leu Glu Glu Lys Phe Gly Phe Lys Val Leu Tyr Ile Asp Thr Asp
            530                 535                 540

Gly Leu Tyr Ala Thr Ile Pro Gly Gly Glu Ser Glu Glu Ile Lys Lys
545                 550                 555                 560

Lys Ala Leu Glu Phe Val Lys Tyr Ile Asn Ser Lys Leu Pro Gly Leu
                565                 570                 575

Leu Glu Leu Glu Tyr Glu Gly Phe Tyr Lys Arg Gly Phe Phe Val Thr
            580                 585                 590

Lys Lys Arg Tyr Ala Val Ile Asp Glu Glu Gly Lys Val Ile Thr Arg
            595                 600                 605

Gly Leu Glu Ile Val Arg Arg Asp Trp Ser Glu Ile Ala Lys Glu Thr
610                 615                 620

Gln Ala Arg Val Leu Glu Thr Ile Leu Lys His Gly Asp Val Glu Glu
625                 630                 635                 640

Ala Val Arg Ile Val Lys Glu Val Ile Gln Lys Leu Ala Asn Tyr Glu
                645                 650                 655

Ile Pro Pro Glu Lys Leu Ala Ile Tyr Glu Gln Ile Thr Arg Pro Leu
                660                 665                 670

His Glu Tyr Lys Ala Ile Gly Pro His Val Ala Val Ala Lys Lys Leu
                675                 680                 685

Ala Ala Lys Gly Val Lys Ile Lys Pro Gly Met Val Ile Gly Tyr Ile
            690                 695                 700

Val Leu Arg Gly Asp Gly Pro Ile Ser Asn Arg Ala Ile Leu Ala Glu
705                 710                 715                 720

Glu Tyr Asp Pro Lys Lys His Lys Tyr Asp Ala Glu Tyr Tyr Ile Glu
                725                 730                 735

Asn Gln Val Leu Pro Ala Val Leu Arg Ile Leu Glu Gly Phe Gly Tyr
                740                 745                 750

Arg Lys Glu Asp Leu Arg Tyr Gln Lys Thr Arg Gln Val Gly Leu Thr
```

```
                  755                 760                 765
Ser Trp Leu Asn Ile Lys Lys Ser
    770                 775

<210> SEQ ID NO 6
<211> LENGTH: 776
<212> TYPE: PRT
<213> ORGANISM: Unknown
<220> FEATURE:
<223> OTHER INFORMATION: Variant derived from Pyrococcus furiosus
      Pfu-Polymerase

<400> SEQUENCE: 6

Met Ala Ile Leu Asp Val Asp Tyr Ile Thr Glu Glu Gly Lys Pro Val
1               5                   10                  15

Ile Arg Leu Phe Lys Lys Glu Asn Gly Lys Phe Lys Ile Glu His Asp
                20                  25                  30

Arg Thr Phe Arg Pro Tyr Ile Tyr Ala Leu Leu Arg Asp Asp Ser Lys
            35                  40                  45

Ile Glu Glu Val Lys Lys Ile Thr Gly Glu Arg His Gly Lys Ile Val
    50                  55                  60

Arg Ile Val Asp Val Glu Lys Val Glu Lys Lys Phe Leu Gly Lys Pro
65                  70                  75                  80

Ile Thr Val Trp Lys Leu Tyr Leu Glu His Pro Gln Asp Arg Pro Thr
                85                  90                  95

Ile Arg Glu Lys Val Arg Glu His Pro Ala Val Val Asp Ile Phe Glu
            100                 105                 110

Tyr Asp Ile Pro Phe Ala Lys Arg Tyr Leu Ile Asp Lys Gly Leu Ile
    115                 120                 125

Pro Met Glu Gly Glu Glu Leu Lys Ile Leu Ala Phe Asp Ile Glu
130                 135                 140

Thr Leu Tyr His Glu Gly Glu Glu Phe Gly Lys Gly Pro Ile Ile Met
145                 150                 155                 160

Ile Ser Tyr Ala Asp Glu Asn Glu Ala Lys Val Ile Thr Trp Lys Asn
                165                 170                 175

Ile Asp Leu Pro Tyr Val Glu Val Val Ser Ser Glu Arg Glu Met Ile
            180                 185                 190

Lys Arg Phe Leu Arg Ile Ile Arg Glu Lys Asp Pro Asp Ile Ile Val
    195                 200                 205

Thr Tyr Asn Gly Asp Ser Phe Asp Phe Pro Tyr Leu Ala Lys Arg Ala
    210                 215                 220

Glu Lys Leu Gly Ile Lys Leu Thr Ile Gly Arg Asp Gly Ser Glu Pro
225                 230                 235                 240

Lys Met Gln Arg Ile Gly Asp Met Thr Ala Val Glu Val Lys Gly Arg
                245                 250                 255

Ile His Phe Asp Leu Tyr His Val Ile Thr Arg Thr Ile Asn Leu Pro
            260                 265                 270

Thr Tyr Thr Leu Glu Ala Val Tyr Glu Ala Ile Phe Gly Lys Pro Lys
    275                 280                 285

Glu Lys Val Tyr Ala Asp Glu Ile Ala Lys Ala Trp Glu Ser Gly Glu
    290                 295                 300

Asn Leu Glu Arg Val Ala Lys Tyr Ser Met Glu Asp Ala Lys Ala Thr
305                 310                 315                 320

Tyr Glu Leu Gly Lys Glu Phe Leu Pro Met Glu Ile Gln Leu Ser Arg
                325                 330                 335

Leu Val Gly Gln Pro Leu Trp Asp Val Ser Arg Ser Ser Thr Gly Asn
```

```
            340             345             350
Leu Val Glu Trp Phe Leu Leu Arg Lys Ala Tyr Glu Arg Asn Glu Val
            355                 360                 365
Ala Pro Asn Lys Pro Ser Glu Glu Tyr Gln Arg Arg Leu Arg Glu
    370                 375                 380
Ser Tyr Thr Gly Gly Phe Val Lys Glu Pro Glu Lys Gly Leu Trp Glu
385                 390                 395                 400
Asn Ile Val Tyr Leu Asp Phe Arg Ala Leu Tyr Pro Ser Ile Ile Ile
                405                 410                 415
Thr His Asn Val Ser Pro Asp Thr Leu Asn Leu Glu Gly Cys Lys Asn
                420                 425                 430
Tyr Asp Ile Ala Pro Gln Val Gly His Lys Phe Cys Lys Asp Ile Pro
            435                 440                 445
Gly Phe Ile Pro Ser Leu Leu Gly His Leu Leu Glu Glu Arg Gln Lys
        450                 455                 460
Ile Lys Thr Lys Met Lys Glu Thr Gln Asp Pro Ile Glu Lys Ile Leu
465                 470                 475                 480
Leu Asp Tyr Arg Gln Lys Ala Ile Lys Leu Leu Ala Asn Ser Phe Tyr
                485                 490                 495
Gly Tyr Tyr Gly Tyr Ala Lys Ala Arg Trp Tyr Cys Lys Glu Cys Ala
            500                 505                 510
Glu Ser Val Thr Ala Trp Gly Arg Lys Tyr Ile Glu Leu Val Trp Lys
            515                 520                 525
Glu Leu Glu Glu Lys Phe Gly Phe Lys Val Leu Tyr Ile Asp Thr Asp
            530                 535                 540
Gly Leu Tyr Ala Thr Ile Pro Gly Gly Glu Ser Glu Glu Ile Lys Lys
545                 550                 555                 560
Lys Ala Leu Glu Phe Val Lys Tyr Ile Asn Ser Lys Leu Pro Gly Leu
                565                 570                 575
Leu Glu Leu Glu Tyr Glu Gly Phe Tyr Lys Arg Gly Phe Phe Val Thr
            580                 585                 590
Lys Lys Arg Tyr Ala Val Ile Asp Glu Glu Gly Lys Val Ile Thr Arg
        595                 600                 605
Gly Leu Glu Ile Val Arg Arg Asp Trp Ser Glu Ile Ala Lys Glu Thr
    610                 615                 620
Gln Ala Arg Val Leu Glu Thr Ile Leu Lys His Gly Asp Val Glu Glu
625                 630                 635                 640
Ala Val Arg Ile Val Lys Glu Val Ile Gln Lys Leu Ala Asn Tyr Glu
                645                 650                 655
Ile Pro Pro Glu Lys Leu Ala Ile Tyr Glu Gln Ile Thr Arg Pro Leu
                660                 665                 670
His Glu Tyr Lys Ala Ile Gly Pro His Val Ala Val Ala Lys Lys Leu
            675                 680                 685
Ala Ala Lys Gly Val Lys Ile Lys Pro Gly Met Val Ile Gly Tyr Ile
        690                 695                 700
Val Leu Arg Gly Asp Gly Pro Ile Ser Asn Arg Ala Ile Leu Ala Glu
705                 710                 715                 720
Glu Tyr Asp Pro Lys Lys His Lys Tyr Asp Ala Glu Tyr Tyr Ile Glu
                725                 730                 735
Asn Gln Val Leu Pro Ala Val Leu Arg Ile Leu Glu Gly Phe Gly Tyr
            740                 745                 750
Arg Lys Glu Asp Leu Arg Tyr Gln Lys Thr Arg Gln Val Gly Leu Thr
        755                 760                 765
```

```
Ser Trp Leu Asn Ile Lys Lys Ser
    770             775
```

```
<210> SEQ ID NO 7
<211> LENGTH: 776
<212> TYPE: PRT
<213> ORGANISM: Unknown
<220> FEATURE:
<223> OTHER INFORMATION: Variant derived from Pyrococcus furiosus
      Pfu-Polymerase

<400> SEQUENCE: 7

Met Ala Ile Leu Asp Val Asp Ala Ile Thr Glu Glu Gly Lys Pro Val
1               5                   10                  15

Ile Arg Leu Phe Lys Lys Glu Asn Gly Lys Phe Lys Ile Glu His Asp
            20                  25                  30

Arg Thr Phe Arg Pro Tyr Ile Tyr Ala Leu Leu Arg Asp Asp Ser Lys
        35                  40                  45

Ile Glu Glu Val Lys Lys Ile Thr Gly Glu Arg His Gly Lys Ile Val
    50                  55                  60

Arg Ile Val Asp Val Glu Lys Val Glu Lys Lys Phe Leu Gly Lys Pro
65                  70                  75                  80

Ile Thr Val Trp Lys Leu Tyr Leu Glu His Pro Gln Asp Val Pro Thr
                85                  90                  95

Ile Arg Glu Lys Val Arg Glu His Pro Ala Val Val Asp Ile Phe Glu
            100                 105                 110

Tyr Asp Arg Pro Phe Ala Lys Arg Tyr Leu Ile Asp Lys Gly Leu Ile
        115                 120                 125

Pro Met Glu Gly Glu Glu Leu Lys Ile Leu Ala Phe Asp Ile Glu
    130                 135                 140

Thr Leu Tyr His Glu Gly Glu Glu Phe Gly Lys Gly Pro Ile Ile Met
145                 150                 155                 160

Ile Ser Tyr Ala Asp Glu Asn Glu Ala Lys Val Ile Thr Trp Lys Asn
                165                 170                 175

Ile Asp Leu Pro Tyr Val Glu Val Val Ser Ser Glu Arg Glu Met Ile
            180                 185                 190

Lys Arg Phe Leu Arg Ile Ile Arg Glu Lys Asp Pro Asp Ile Ile Val
        195                 200                 205

Thr Tyr Asn Gly Asp Ser Phe Asp Phe Pro Tyr Leu Ala Lys Arg Ala
    210                 215                 220

Glu Lys Leu Gly Ile Lys Leu Thr Ile Gly Arg Asp Gly Ser Glu Pro
225                 230                 235                 240

Lys Met Gln Arg Ile Gly Asp Met Thr Ala Val Glu Val Lys Gly Arg
                245                 250                 255

Ile His Phe Asp Leu Tyr His Val Ile Thr Arg Thr Ile Asn Leu Pro
            260                 265                 270

Thr Tyr Thr Leu Glu Ala Val Tyr Glu Ala Ile Phe Gly Lys Pro Lys
        275                 280                 285

Glu Lys Val Tyr Ala Asp Glu Ile Ala Lys Ala Trp Glu Ser Gly Glu
    290                 295                 300

Asn Leu Glu Arg Val Ala Lys Tyr Ser Met Glu Asp Ala Lys Ala Thr
305                 310                 315                 320

Tyr Glu Leu Gly Lys Glu Phe Leu Pro Met Glu Ile Gln Leu Ser Arg
                325                 330                 335

Leu Val Gly Gln Pro Leu Trp Asp Val Ser Arg Ser Ser Thr Gly Asn
            340                 345                 350
```

```
Leu Val Glu Trp Phe Leu Leu Arg Lys Ala Tyr Glu Arg Asn Glu Val
            355                 360                 365

Ala Pro Asn Lys Pro Ser Glu Glu Tyr Gln Arg Arg Leu Arg Glu
370                 375                 380

Ser Tyr Thr Gly Gly Phe Val Lys Glu Pro Glu Lys Gly Leu Trp Glu
385                 390                 395                 400

Asn Ile Val Tyr Leu Asp Phe Arg Ala Leu Tyr Pro Ser Ile Ile Ile
                405                 410                 415

Thr His Asn Val Ser Pro Asp Thr Leu Asn Leu Glu Gly Cys Lys Asn
                420                 425                 430

Tyr Asp Ile Ala Pro Gln Val Gly His Lys Phe Cys Lys Asp Ile Pro
                435                 440                 445

Gly Phe Ile Pro Ser Leu Leu Gly His Leu Leu Glu Glu Arg Gln Lys
450                 455                 460

Ile Lys Thr Lys Met Lys Glu Thr Gln Asp Pro Ile Glu Lys Ile Leu
465                 470                 475                 480

Leu Asp Tyr Arg Gln Lys Ala Ile Lys Leu Leu Ala Asn Ser Phe Tyr
                485                 490                 495

Gly Tyr Tyr Gly Tyr Ala Lys Ala Arg Trp Tyr Cys Lys Glu Cys Ala
                500                 505                 510

Glu Ser Val Thr Ala Trp Gly Arg Lys Tyr Ile Glu Leu Val Trp Lys
                515                 520                 525

Glu Leu Glu Glu Lys Phe Gly Phe Lys Val Leu Tyr Ile Asp Thr Asp
530                 535                 540

Gly Leu Tyr Ala Thr Ile Pro Gly Gly Glu Ser Glu Glu Ile Lys Lys
545                 550                 555                 560

Lys Ala Leu Glu Phe Val Lys Tyr Ile Asn Ser Lys Leu Pro Gly Leu
                565                 570                 575

Leu Glu Leu Glu Tyr Glu Gly Phe Tyr Lys Arg Gly Phe Phe Val Thr
                580                 585                 590

Lys Lys Arg Tyr Ala Val Ile Asp Glu Glu Gly Lys Val Ile Thr Arg
                595                 600                 605

Gly Leu Glu Ile Val Arg Arg Asp Trp Ser Glu Ile Ala Lys Glu Thr
610                 615                 620

Gln Ala Arg Val Leu Glu Thr Ile Leu Lys His Gly Asp Val Glu Glu
625                 630                 635                 640

Ala Val Arg Ile Val Lys Glu Val Ile Gln Lys Leu Ala Asn Tyr Glu
                645                 650                 655

Ile Pro Pro Glu Lys Leu Ala Ile Tyr Glu Gln Ile Thr Arg Pro Leu
                660                 665                 670

His Glu Tyr Lys Ala Ile Gly Pro His Val Ala Val Ala Lys Lys Leu
                675                 680                 685

Ala Ala Lys Gly Val Lys Ile Lys Pro Gly Met Val Ile Gly Tyr Ile
690                 695                 700

Val Leu Arg Gly Asp Gly Pro Ile Ser Asn Arg Ala Ile Leu Ala Glu
705                 710                 715                 720

Glu Tyr Asp Pro Lys Lys His Lys Tyr Asp Ala Glu Tyr Tyr Ile Glu
                725                 730                 735

Asn Gln Val Leu Pro Ala Val Leu Arg Ile Leu Glu Gly Phe Gly Tyr
                740                 745                 750

Arg Lys Glu Asp Leu Arg Tyr Gln Lys Thr Arg Gln Val Gly Leu Thr
                755                 760                 765

Ser Trp Leu Asn Ile Lys Lys Ser
770                 775
```

<210> SEQ ID NO 8
<211> LENGTH: 776
<212> TYPE: PRT
<213> ORGANISM: Unknown
<220> FEATURE:
<223> OTHER INFORMATION: Variant derived from Pyrococcus furiosus
      Pfu-Polymerase

<400> SEQUENCE: 8

```
Met Ala Ile Leu Asp Val Asp Tyr Ile Thr Glu Glu Gly Lys Pro Val
1               5                   10                  15

Ile Arg Leu Phe Lys Lys Glu Asn Gly Lys Phe Lys Ile Glu His Asp
            20                  25                  30

Arg Thr Phe Arg Pro Ala Ile Tyr Ala Leu Leu Arg Asp Asp Ser Lys
        35                  40                  45

Ile Glu Glu Val Lys Lys Ile Thr Gly Glu Arg His Gly Lys Ile Val
    50                  55                  60

Arg Ile Val Asp Val Glu Lys Val Glu Lys Lys Phe Leu Gly Lys Pro
65                  70                  75                  80

Ile Thr Val Trp Lys Leu Tyr Leu Glu His Pro Gln Asp Val Pro Thr
                85                  90                  95

Ile Arg Glu Lys Val Arg Glu His Pro Ala Val Val Asp Ile Phe Glu
            100                 105                 110

Tyr Asp Gln Pro Phe Ala Lys Arg Tyr Leu Ile Asp Lys Gly Leu Ile
        115                 120                 125

Pro Met Glu Gly Glu Glu Leu Lys Ile Leu Ala Phe Asp Ile Glu
    130                 135                 140

Thr Leu Tyr His Glu Gly Glu Glu Phe Gly Lys Gly Pro Ile Ile Met
145                 150                 155                 160

Ile Ser Tyr Ala Asp Glu Asn Glu Ala Lys Val Ile Thr Trp Lys Asn
                165                 170                 175

Ile Asp Leu Pro Tyr Val Glu Val Val Ser Ser Glu Arg Glu Met Ile
            180                 185                 190

Lys Arg Phe Leu Arg Ile Ile Arg Glu Lys Asp Pro Asp Ile Ile Val
        195                 200                 205

Thr Tyr Asn Gly Asp Ser Phe Asp Phe Pro Tyr Leu Ala Lys Arg Ala
    210                 215                 220

Glu Lys Leu Gly Ile Lys Leu Thr Ile Gly Arg Asp Gly Ser Glu Pro
225                 230                 235                 240

Lys Met Gln Arg Ile Gly Asp Met Thr Ala Val Glu Val Lys Gly Arg
                245                 250                 255

Ile His Phe Asp Leu Tyr His Val Ile Thr Arg Thr Ile Asn Leu Pro
            260                 265                 270

Thr Tyr Thr Leu Glu Ala Val Tyr Glu Ala Ile Phe Gly Lys Pro Lys
        275                 280                 285

Glu Lys Val Tyr Ala Asp Glu Ile Ala Lys Ala Trp Glu Ser Gly Glu
    290                 295                 300

Asn Leu Glu Arg Val Ala Lys Tyr Ser Met Glu Asp Ala Lys Ala Thr
305                 310                 315                 320

Tyr Glu Leu Gly Lys Glu Phe Leu Pro Met Glu Ile Gln Leu Ser Arg
                325                 330                 335

Leu Val Gly Gln Pro Leu Trp Asp Val Ser Arg Ser Ser Thr Gly Asn
            340                 345                 350

Leu Val Glu Trp Phe Leu Leu Arg Lys Ala Tyr Glu Arg Asn Glu Val
        355                 360                 365
```

```
Ala Pro Asn Lys Pro Ser Glu Glu Tyr Gln Arg Arg Leu Arg Glu
    370                 375                 380

Ser Tyr Thr Gly Gly Phe Val Lys Glu Pro Glu Lys Gly Leu Trp Glu
385                 390                 395                 400

Asn Ile Val Tyr Leu Asp Phe Arg Ala Leu Tyr Pro Ser Ile Ile Ile
                405                 410                 415

Thr His Asn Val Ser Pro Asp Thr Leu Asn Leu Glu Gly Cys Lys Asn
            420                 425                 430

Tyr Asp Ile Ala Pro Gln Val Gly His Lys Phe Cys Lys Asp Ile Pro
        435                 440                 445

Gly Phe Ile Pro Ser Leu Leu Gly His Leu Leu Glu Glu Arg Gln Lys
    450                 455                 460

Ile Lys Thr Lys Met Lys Glu Thr Gln Asp Pro Ile Glu Lys Ile Leu
465                 470                 475                 480

Leu Asp Tyr Arg Gln Lys Ala Ile Lys Leu Leu Ala Asn Ser Phe Tyr
                485                 490                 495

Gly Tyr Tyr Gly Tyr Ala Lys Ala Arg Trp Tyr Cys Lys Glu Cys Ala
            500                 505                 510

Glu Ser Val Thr Ala Trp Gly Arg Lys Tyr Ile Glu Leu Val Trp Lys
        515                 520                 525

Glu Leu Glu Glu Lys Phe Gly Phe Lys Val Leu Tyr Ile Asp Thr Asp
    530                 535                 540

Gly Leu Tyr Ala Thr Ile Pro Gly Gly Glu Ser Glu Glu Ile Lys Lys
545                 550                 555                 560

Lys Ala Leu Glu Phe Val Lys Tyr Ile Asn Ser Lys Leu Pro Gly Leu
                565                 570                 575

Leu Glu Leu Glu Tyr Glu Gly Phe Tyr Lys Arg Gly Phe Phe Val Thr
            580                 585                 590

Lys Lys Arg Tyr Ala Val Ile Asp Glu Glu Gly Lys Val Ile Thr Arg
        595                 600                 605

Gly Leu Glu Ile Val Arg Arg Asp Trp Ser Glu Ile Ala Lys Glu Thr
    610                 615                 620

Gln Ala Arg Val Leu Glu Thr Ile Leu Lys His Gly Asp Val Glu Glu
625                 630                 635                 640

Ala Val Arg Ile Val Lys Glu Val Ile Gln Lys Leu Ala Asn Tyr Glu
                645                 650                 655

Ile Pro Pro Glu Lys Leu Ala Ile Tyr Glu Gln Ile Thr Arg Pro Leu
            660                 665                 670

His Glu Tyr Lys Ala Ile Gly Pro His Val Ala Val Ala Lys Lys Leu
        675                 680                 685

Ala Ala Lys Gly Val Lys Ile Lys Pro Gly Met Val Ile Gly Tyr Ile
    690                 695                 700

Val Leu Arg Gly Asp Gly Pro Ile Ser Asn Arg Ala Ile Leu Ala Glu
705                 710                 715                 720

Glu Tyr Asp Pro Lys Lys His Lys Tyr Asp Ala Glu Tyr Tyr Ile Glu
                725                 730                 735

Asn Gln Val Leu Pro Ala Val Leu Arg Ile Leu Glu Gly Phe Gly Tyr
            740                 745                 750

Arg Lys Glu Asp Leu Arg Tyr Gln Lys Thr Arg Gln Val Gly Leu Thr
        755                 760                 765

Ser Trp Leu Asn Ile Lys Lys Ser
    770                 775
```

<210> SEQ ID NO 9
<211> LENGTH: 2328
<212> TYPE: DNA
<213> ORGANISM: Unknown
<220> FEATURE:
<223> OTHER INFORMATION: Variant derived from Pyrococcus furiosus
Pfu-Polymerase

<400> SEQUENCE: 9

| | | | | | |
|---|---|---|---|---|---|
| atggctatcc | tggacgttga | cgccatcacc | gaagaaggta | agccggttat | ccgtctgttc | 60 |
| aaaaaagaaa | acgtaaaatt | caaaatcgaa | cacgaccgta | ccttccgtcc | gtacatctac | 120 |
| gctctgctgc | gtgacgactc | taaaatcgaa | gaagttaaaa | aaatcaccgg | tgaacgtcat | 180 |
| ggaaagattg | tgagaattgt | tgatgtagag | aaggttgaga | aaagtttct | cggcaagcct | 240 |
| attaccgtgt | ggaaacttta | tttggaacat | ccccaagatg | ttcccactat | tagagaaaaa | 300 |
| gttagagaac | atccagcagt | tgtggacatc | ttcgaatacg | atattccatt | tgcaaagaga | 360 |
| tacctcatcg | acaaaggcct | aataccaatg | gaggggaag | aagagctaaa | gattcttgcc | 420 |
| ttcgatatag | aaaccctcta | tcacgaagga | gaagagtttg | aaaaggccc | aattataatg | 480 |
| attagttatg | cagatgaaaa | tgaagcaaag | gtgattactt | ggaaaaacat | agatcttcca | 540 |
| tacgttgagg | ttgtatcaag | cgagagagag | atgataaaga | gatttctcag | gattatcagg | 600 |
| gagaaggatc | ctgacattat | agttacttat | aatggagact | cattcgactt | cccatattta | 660 |
| gcgaaaaggg | cagaaaaact | tgggattaaa | ttaaccattg | aagagatgg | aagcgagccc | 720 |
| aagatgcaga | gaataggcga | tatgacggct | gtagaagtca | agggaagaat | acattcgac | 780 |
| ttgtatcatg | taataacaag | gacaataaat | ctcccaacat | acacactaga | ggctgtatat | 840 |
| gaagcaattt | ttggaaagcc | aaaggagaag | gtatacgccg | acgagatagc | aaaagcctgg | 900 |
| gaaagtggag | agaaccttga | gagagttgcc | aaatactcga | tggaagatgc | aaaggcaact | 960 |
| tatgaactcg | ggaaagaatt | ccttccaatg | gaaattcagc | tttcaagatt | agttggacaa | 1020 |
| cctttatggg | atgtttcaag | gtcaagcaca | gggaaccttg | tagagtggtt | cttacttagg | 1080 |
| aaagcctacg | aaagaaacga | agtagctcca | aacaagccaa | gtgaagagga | gtatcaaaga | 1140 |
| aggctcaggg | agagctacac | aggtggattc | gttaagagc | cagaaaaggg | gttgtgggaa | 1200 |
| aacatagtat | acctagattt | tagagcccta | tatcccctcga | ttataattac | ccacaatgtt | 1260 |
| tctcccgata | ctctaaatct | tgagggatgc | aagaactatg | atatcgctcc | tcaagtaggc | 1320 |
| cacaagttct | gcaaggacat | ccctggtttt | ataccaagtc | tcttgggaca | tttgttagag | 1380 |
| gaaagacaaa | agattaagac | aaaaatgaag | gaaactcaag | atcctataga | aaaaatactc | 1440 |
| cttgactata | gacaaaaagc | gataaaactc | ttagcaaatt | cttctacgg | atattatggc | 1500 |
| tatgcaaaag | caagatggta | ctgtaaggag | tgtgctgaga | gcgttactgc | ctggggaaga | 1560 |
| aagtacatcg | agttagtatg | gaaggagctc | gaagaaaagt | ttggatttaa | agtcctctac | 1620 |
| attgacactg | atggtctcta | tgcaactatc | ccaggaggaa | aaagtgagga | aataaagaaa | 1680 |
| aaggctctag | aatttgtaaa | atacataaat | tcaaagctcc | ctggactgct | agagcttgaa | 1740 |
| tatgaagggt | tttataagag | gggattcttc | gttacgaaga | agaggtatgc | agtaatagat | 1800 |
| gaagaaggaa | aagtcattac | tcgtggttta | gagatagtta | ggagagattg | gagtgaaatt | 1860 |
| gcaaaagaaa | ctcaagctag | agttttggag | acaatactaa | aacacggaga | tgttgaagaa | 1920 |
| gctgtgagaa | tagtaaaaga | agtaatacaa | aagcttgcca | attatgaaat | tccaccagag | 1980 |
| aagctcgcaa | tatatgagca | gataacaaga | ccattcatg | agtataaggc | gataggtcct | 2040 |
| cacgtagctg | ttgcaaagaa | actagctgct | aaaggagtta | aaataaagcc | aggaatggta | 2100 |

-continued

```
attggataca tagtacttag aggcgatggt ccaattagca ataggcaat tctagctgag      2160 gaatacgatc ccaaaaagca caagtatgac gcagaatatt acattgagaa ccaggttctt     2220
ccagcggtac ttaggatatt ggagggattt ggatacagaa aggaagacct cagataccaa     2280
aagacaagac aagtcggcct aacttcctgg cttaacatta aaaaatcc                  2328
```

<210> SEQ ID NO 10
<211> LENGTH: 2328
<212> TYPE: DNA
<213> ORGANISM: Unknown
<220> FEATURE:
<223> OTHER INFORMATION: Variant derived from Pyrococcus furiosus Pfu-Polymerase

<400> SEQUENCE: 10

```
atggctatcc tggacgttga ctacatcacc gaagaaggta agccggttat ccgtctgttc       60
aaaaaagaaa acggtaaatt caaaatcgaa cacgaccgta ccttccgtcc gtacatctac      120
gctctgctgc gtgacgactc taaaatcgaa gaagttaaaa aaatcaccgg tgaacgtcat      180
ggaaagattg tgagaattgt tgatgtagag aaggttgaga aaagtttct cggcaagcct       240 attccgtgt ggaaacttta tttgaacat ccccaagatc agcccactat tagagaaaaa        300
gttagagaac atccagcagt tgtggacatc ttcgaatacg atattccatt tgcaaagaga      360
tacctcatcg acaaaggcct aataccaatg gaggggaag aagagctaaa gattcttgcc       420
ttcgatatag aaacccctcta tcacgaagga gaagagtttg gaaaaggccc aattataatg     480
attagttatg cagatgaaaa tgaagcaaag gtgattactt ggaaaaacat agatcttcca      540
tacgttgagg ttgtatcaag cgagagagag atgataaaga gatttctcag gattatcagg      600
gagaaggatc ctgacattat agttacttat aatggagact cattcgactt cccatattta      660 gcgaaaggg cagaaaaact tgggattaaa ttaaccattg gaagagatgg aagcgagccc       720
aagatgcaga gaataggcga tatgacggct gtagaagtca agggaagaat acatttcgac      780
ttgtatcatg taataacaag gacaataaat ctcccaacat acacactaga ggctgtatat      840
gaagcaattt ttggaaagcc aaaggagaag gtatacgccg acgagatagc aaaagcctgg     900
gaaagtggag agaaccttga gagttgcc aaatactcga tggaagatgc aaaggcaact       960
tatgaactcg ggaagaatt ccttccaatg gaaattcagc tttcaagatt agttggacaa     1020
cctttatggg atgtttcaag gtcaagcaca gggaaccttg tagagtggtt cttacttagg    1080
aaagcctacg aaagaaacga gtagctcca aacaagccaa gtgaagagga gtatcaaaga    1140
aggctcaggg agagctacac aggtggattc gttaaagagc cagaaaaggg gttgtgggaa   1200
aacatagtat acctagattt tagagcccta tatccctcga ttataattac ccacaatgtt    1260
tctcccgata ctctaaatct tgagggatgc aagaactatg atatcgctcc tcaagtaggc    1320
cacaagttct gcaaggacat ccctggtttt ataccaagtc tcttgggaca tttgttagag   1380
gaaagacaaa agattaagac aaaaatgaag gaaactcaag atcctataga aaaaatactc   1440
cttgactata gacaaaaagc gataaaactc ttagcaaatt cttttctacgg atattatggc    1500 tatgcaaaag caagatggta ctgtaaggag tgtgctgaga gcgttactgc tggggaaga     1560 aagtacatcg agttagtatg gaaggagctc gaagaaaagt ttggatttaa agtcctctac    1620
attgacactg atggtctcta tgcaactatc ccaggaggag aaagtgagga ataaagaaa     1680 aaggctctag aatttgtaaa atacataaat tcaaagctcc ctggactgct agagcttgaa    1740 tatgaaggt tttataagag gggattcttc gttacgaaga gaggtatgc agtaatgat      1800 gaagaaggaa aagtcattac tcgtggttta gagatagtta ggagagattg gagtgaaatt   1860
```

```
gcaaaagaaa ctcaagctag agttttggag acaatactaa acacggaga tgttgaagaa    1920 gctgtgagaa tagtaaaaga agtaatacaa aagcttgcca attatgaaat tccaccagag   1980
aagctcgcaa tatatgagca gataacaaga ccattacatg agtataaggc gataggtcct   2040
cacgtagctg ttgcaaagaa actagctgct aaaggagtta aaataaagcc aggaatggta   2100
attggataca tagtacttag aggcgatggt ccaattagca ataggggaat tctagctgag   2160
gaatacgatc ccaaaaagca caagtatgac gcagaatatt acattgagaa ccaggttctt   2220
ccagcggtac ttaggatatt ggagggattt ggatacagaa aggaagacct cagataccaa   2280
aagacaagac aagtcggcct aacttcctgg cttaacatta aaaaatcc                2328
```

<210> SEQ ID NO 11
<211> LENGTH: 2325
<212> TYPE: DNA
<213> ORGANISM: Unknown
<220> FEATURE:
<223> OTHER INFORMATION: Variant derived from Pyrococcus furiosus
      Pfu-Polymerase

<400> SEQUENCE: 11

```
atggctatcc tggacgttga ctacatcacc gaagaaggta agccggttat ccgtctgttc     60
aaaaaagaaa acggtaaatt caaaatcgaa cacgaccgta ccttccgtcc gtacatctac    120
gctctgctgc gtgacgactc taaaatcgaa gaagttaaaa aaatcaccgg tgaacgtcat    180
ggaaagattg tgagaattgt tgatgtgagg aaggttgaga aaagtttcct cggcaagcct    240
attaccgtgt ggaaacttta tttggaacat ccccaagatg ttcccactat tagagaaaaa    300
gttagagaac atccagcagt tgtggacatc ttcgaatacg atatttttgc aaagagatac    360
ctcatcgaca aaggcctaat accaatggag ggggaagaag agctaaagat tcttgccttc    420
gatatagaaa ccctctatca cgaaggagaa gagtttggaa aagcccaat ataatgatt     480 agttatgcag atgaaaatga agcaaggtg attacttgga aaaacataga tcttccatac    540
gttgaggttg tatcaagcga gagagagatg ataaagagat ttctcaggat tatcagggag    600
aaggatcctg acattatagt tacttataat ggagactcat tcgactttcc atatttagcg    660 aaaaggggcag aaaacttggg gattaaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840 gcaattttg gaaagccaaa ggagaaggta tacgccgacg agatagcaaa agcctgggaa    900
agtggagaga accttgagag agttgccaaa tactcgatgg aagatgcaaa ggcaacttat    960
gaactcggga agaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcaggagaa gctacacagg tggattcgtt aaagagccag aaaagggggtt gtgggaaaac   1200 atagtatacc tagattttag agccctatat ccctcgatta taattcccca caatgttttct   1260 cccgatactc taaatcttga gggatgcaag aactatgata tcgctcctca gtaggccac     1320 aagttctgca aggacatccc tggttttata ccaagtctct tgggacattt gttagaggaa   1380
agacaaaaga ttaagacaaa aatgaaggaa actcaagatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg gggaagaaag   1560
```

```
tacatcgagt tagtatggaa ggagctcgaa gaaaagtttg gatttaaagt cctctacatt    1620
gacactgatg gtctctatgc aactatccca ggaggagaaa gtgaggaaat aaagaaaaag    1680
gctctagaat ttgtaaaata cataaattca aagctccctg gactgctaga gcttgaatat    1740
gaagggtttt ataagagggg attcttcgtt acgaagaaga ggtatgcagt aatagatgaa    1800
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaaagaagt aatacaaaag cttgccaatt atgaaattcc accagagaag    1980
ctcgcaatat atgagcagat aacaagacca ttacatgagt ataaggcgat aggtcctcac    2040
gtagctgttg caaagaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca ttgagaacca ggttcttcca    2220
gcggtactta ggatattgga gggatttgga tacagaaagg aagacctcag ataccaaaag    2280
acaagacaag tcggcctaac ttcctggctt aacattaaaa aatcc                   2325
```

<210> SEQ ID NO 12
<211> LENGTH: 130
<212> TYPE: PRT
<213> ORGANISM: Thermococcus gorgonarius

<400> SEQUENCE: 12

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu
    130
```

<210> SEQ ID NO 13
<211> LENGTH: 103
<212> TYPE: PRT
<213> ORGANISM: Unknown
<220> FEATURE:
<223> OTHER INFORMATION: Family B DNA polymerase encoded by RB69
      bacteriophage

<400> SEQUENCE: 13

```
Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45
```

```
Tyr Phe Asp Ile Tyr Gly Lys Pro Cys Thr Arg Lys Leu Phe Ala Asn
        50                  55                  60

Met Arg Asp Ala Ser Gln Trp Ile Lys Arg Met Glu Asp Ile Gly Leu
 65                  70                  75                  80

Glu Ala Leu Gly Met Asp Phe Lys Leu Ala Tyr Leu Ser Asp Thr
                 85                  90                  95

Tyr Asn Tyr Glu Ile Lys Tyr
                100

<210> SEQ ID NO 14
<211> LENGTH: 24
<212> TYPE: DNA
<213> ORGANISM: Unknown
<220> FEATURE:
<223> OTHER INFORMATION: Artificial Primer

<400> SEQUENCE: 14
ggggatcctc tagagtcgac ctgc                                          24

<210> SEQ ID NO 15
<211> LENGTH: 44
<212> TYPE: DNA
<213> ORGANISM: Unknown
<220> FEATURE:
<223> OTHER INFORMATION: Artificial Template

<400> SEQUENCE: 15
ggagacaagc ttguatgcct gcaggtcgac tctagcggct aaaa                    44

<210> SEQ ID NO 16
<211> LENGTH: 22
<212> TYPE: DNA
<213> ORGANISM: Unknown
<220> FEATURE:
<223> OTHER INFORMATION: Artificial Oligodeoxynucleotide

<400> SEQUENCE: 16
gcccgcggga uatcggccct ta                                            22

<210> SEQ ID NO 17
<211> LENGTH: 44
<212> TYPE: DNA
<213> ORGANISM: Unknown
<220> FEATURE:
<223> OTHER INFORMATION: Artificial Template

<400> SEQUENCE: 17
ggagacaagc ttgtatgcct gcaggtcgac tctagcggct aaaa                    44

<210> SEQ ID NO 18
<211> LENGTH: 131
<212> TYPE: PRT
<213> ORGANISM: Pyrococcus furiosus

<400> SEQUENCE: 18

Met Ile Leu Asp Val Asp Tyr Ile Thr Glu Glu Gly Lys Pro Val Ile
  1               5                  10                  15

Arg Leu Phe Lys Lys Glu Asn Gly Lys Phe Lys Ile Glu His Asp Arg
                 20                  25                  30

Thr Phe Arg Pro Tyr Ile Tyr Ala Leu Leu Arg Asp Asp Ser Lys Ile
             35                  40                  45

Glu Glu Val Lys Lys Ile Thr Gly Glu Arg His Gly Lys Ile Val Arg
 50                  55                  60
```

```
Ile Val Asp Val Glu Lys Val Glu Lys Phe Leu Gly Lys Pro Ile
 65                  70                  75                  80

Thr Val Trp Lys Leu Tyr Leu Glu His Pro Gln Asp Val Pro Thr Ile
                 85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly
    130

<210> SEQ ID NO 19
<211> LENGTH: 131
<212> TYPE: PRT
<213> ORGANISM: Thermococcus gorgonarius

<400> SEQUENCE: 19

Met Ile Leu Asp Thr Asp Tyr Ile Thr Glu Asp Gly Lys Pro Val Ile
  1               5                  10                  15

Arg Ile Phe Lys Lys Glu Asn Gly Glu Phe Lys Ile Asp Tyr Asp Arg
                 20                  25                  30

Asn Phe Glu Pro Tyr Ile Tyr Ala Leu Leu Lys Asp Asp Ser Ala Ile
            35                  40                  45

Glu Asp Val Lys Lys Ile Thr Ala Glu Arg His Gly Thr Thr Val Arg
 50                  55                  60

Val Val Arg Ala Glu Lys Val Lys Lys Phe Leu Gly Arg Pro Ile
 65                  70                  75                  80

Glu Val Trp Lys Leu Tyr Phe Thr His Pro Gln Asp Val Pro Ala Ile
                 85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly
    130

<210> SEQ ID NO 20
<211> LENGTH: 131
<212> TYPE: PRT
<213> ORGANISM: Pyrococcus kodakaraensis

<400> SEQUENCE: 20

Met Ile Leu Asp Thr Asp Tyr Ile Thr Glu Asp Gly Lys Pro Val Ile
  1               5                  10                  15

Arg Ile Phe Lys Lys Glu Asn Gly Glu Phe Lys Ile Glu Tyr Asp Arg
                 20                  25                  30

Thr Phe Glu Pro Tyr Phe Tyr Ala Leu Leu Lys Asp Asp Ser Ala Ile
            35                  40                  45

Glu Glu Val Lys Lys Ile Thr Ala Glu Arg His Gly Thr Val Val Thr
 50                  55                  60

Val Lys Arg Val Glu Lys Val Gln Lys Phe Leu Gly Arg Pro Val
 65                  70                  75                  80

Glu Val Trp Lys Leu Tyr Phe Thr His Pro Gln Asp Val Pro Ala Ile
                 85                  90                  95

Arg Asp Lys Ile Arg Glu His Pro Ala Val Ile Asp Ile Tyr Glu Tyr
            100                 105                 110
```

```
Asp Ile Pro Glu Ala Lys Arg Tyr Leu Ile Asp Lys Gly Leu Val Pro
            115                 120                 125
Met Glu Gly
    130

<210> SEQ ID NO 21
<211> LENGTH: 131
<212> TYPE: PRT
<213> ORGANISM: Desulfurococcus Tok

<400> SEQUENCE: 21

Met Ile Leu Asp Ala Asp Tyr Ile Thr Glu Asp Gly Lys Pro Val Ile
1               5                   10                  15
Arg Val Phe Lys Lys Glu Lys Gly Glu Phe Lys Ile Asp Tyr Asp Arg
                20                  25                  30
Asp Phe Glu Pro Tyr Ile Tyr Ala Leu Leu Lys Asp Asp Ser Ala Ile
            35                  40                  45
Glu Asp Ile Lys Lys Ile Thr Ala Glu Arg His Gly Thr Thr Val Arg
    50                  55                  60
Val Thr Arg Ala Glu Arg Val Lys Lys Phe Leu Gly Arg Pro Val
65                  70                  75                  80
Glu Val Trp Lys Leu Tyr Phe Thr His Pro Gln Asp Val Pro Ala Ile
                85                  90                  95
Arg Asp Lys Ile Arg Glu His Pro Ala Val Val Asp Ile Tyr Glu Tyr
            100                 105                 110
Asp Ile Pro Phe Ala Lys Arg Tyr Leu Ile Asp Arg Gly Leu Ile Pro
            115                 120                 125
Met Glu Gly
    130

<210> SEQ ID NO 22
<211> LENGTH: 132
<212> TYPE: PRT
<213> ORGANISM: Thermococcus sp. 9°N-7

<400> SEQUENCE: 22

Met Ile Leu Asp Thr Asp Tyr Ile Thr Glu Asn Gly Lys Pro Val Ile
1               5                   10                  15
Arg Val Phe Lys Lys Glu Asn Gly Glu Phe Lys Ile Glu Tyr Asp Arg
                20                  25                  30
Thr Phe Glu Pro Tyr Phe Tyr Ala Leu Leu Lys Asp Asp Ser Ala Ile
            35                  40                  45
Glu Asp Val Lys Lys Val Thr Ala Lys Arg His Gly Thr Val Val Lys
    50                  55                  60
Val Lys Arg Ala Glu Lys Val Gln Lys Lys Phe Leu Gly Arg Pro
65                  70                  75                  80
Ile Glu Val Trp Lys Leu Tyr Phe Asn His Pro Gln Asp Val Pro Ala
                85                  90                  95
Ile Arg Asp Arg Ile Arg Ala His Pro Ala Val Val Asp Ile Tyr Glu
            100                 105                 110
Tyr Asp Ile Pro Phe Ala Lys Arg Tyr Leu Ile Asp Lys Gly Leu Ile
            115                 120                 125
Pro Met Glu Gly
    130

<210> SEQ ID NO 23
<211> LENGTH: 131
<212> TYPE: PRT
```

<213> ORGANISM: Thermococcus litoralis

<400> SEQUENCE: 23

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
                20                  25                  30

His Phe Gln Pro Tyr Ile Tyr Ala Leu Leu Lys Asp Asp Ser Ala Ile
            35                  40                  45

Glu Glu Ile Lys Ala Ile Lys Gly Glu Arg His Gly Lys Thr Val Arg
        50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly
    130

<210> SEQ ID NO 24
<211> LENGTH: 161
<212> TYPE: PRT
<213> ORGANISM: Methanococcus voltae

<400> SEQUENCE: 24

Met Asp Leu Asp Tyr Asn Ser Lys Asp Leu Cys Ile Asp Met Tyr Tyr
1               5                   10                  15

Lys Asn Cys Gly Leu Lys Lys Pro Glu Ile Asn Leu Gln Lys Glu Cys
                20                  25                  30

Glu Phe Lys Pro Tyr Phe Tyr Val Asp Thr Ser Glu Pro Lys Glu Ile
            35                  40                  45

Tyr Asp Tyr Leu Asp Gly Leu Asn Gln Glu Ile Asp Leu Lys Lys Leu
        50                  55                  60

Glu Pro Glu Phe Glu Asn Asn Thr Ser Leu Lys Val Gln Asp Leu Ile
65                  70                  75                  80

Thr Asn Ile Glu Ile Ile Glu Lys Ile Val Tyr Ser Asp Tyr Ile Leu
                85                  90                  95

Asn Gly Lys Asp Ile Ser Glu Val Ser Asp Phe Lys Asn Lys Lys Glu
                100                 105                 110

Arg Lys Ile Cys Lys Val Tyr Val Lys Tyr Pro Asn His Val Lys Ile
            115                 120                 125

Ile Arg Glu Tyr Phe Lys Glu Phe Gly Lys Ser Tyr Glu Phe Asp Ile
        130                 135                 140

Pro Phe Leu Arg Arg Tyr Met Ile Asp Gln Asp Ile Val Pro Ser Ala
145                 150                 155                 160

Lys

<210> SEQ ID NO 25
<211> LENGTH: 132
<212> TYPE: PRT
<213> ORGANISM: Pyrobaculum islandicum

<400> SEQUENCE: 25

Met Glu Leu Lys Val Trp Pro Leu Asp Ile Thr Tyr Ala Val Val Gly

-continued

```
                 1               5              10              15
Ser Val Pro Glu Ile Arg Ile Phe Gly Ile Leu Ser Ser Gly Glu Arg
                20              25              30

Val Val Leu Ile Asp Arg Ser Phe Lys Pro Tyr Phe Tyr Val Asp Cys
                35              40              45

Ala Val Cys Glu Pro Ala Ala Leu Lys Thr Ala Leu Ser Arg Val Ala
 50              55              60

Pro Ile Asp Asp Val Gln Ile Val Glu Arg Arg Phe Leu Gly Arg Ser
 65              70              75              80

Lys Lys Phe Leu Lys Val Ile Ala Lys Ile Pro Glu Asp Val Arg Lys
                85              90              95

Leu Arg Glu Ala Ala Met Ser Ile Pro Arg Val Ser Gly Val Tyr Glu
                100             105             110

Ala Asp Ile Arg Phe Tyr Met Arg Tyr Met Ile Asp Met Gly Val Val
                115             120             125

Pro Cys Ser Trp
                130
```

<210> SEQ ID NO 26
<211> LENGTH: 131
<212> TYPE: PRT
<213> ORGANISM: Archaeoglobus fulgidus

<400> SEQUENCE: 26

```
Met Glu Arg Val Glu Gly Trp Leu Ile Asp Ala Asp Tyr Glu Thr Ile
 1               5              10              15

Gly Gly Lys Ala Val Val Arg Leu Trp Cys Lys Asp Asp Gln Gly Ile
                20              25              30

Phe Val Ala Tyr Asp Tyr Asn Phe Asp Pro Tyr Phe Tyr Val Ile Gly
                35              40              45

Val Asp Glu Asp Ile Leu Lys Asn Ala Ala Thr Ser Thr Arg Arg Glu
 50              55              60

Val Ile Lys Leu Lys Ser Phe Glu Lys Ala Gln Leu Lys Thr Leu Gly
 65              70              75              80

Arg Glu Val Glu Gly Tyr Ile Val Tyr Ala His His Pro Gln His Val
                85              90              95

Pro Lys Leu Arg Asp Tyr Leu Ser Gln Phe Gly Asp Val Arg Glu Ala
                100             105             110

Asp Ile Pro Phe Ala Tyr Arg Tyr Leu Ile Asp Lys Asp Leu Ala Cys
                115             120             125

Met Asp Gly
                130
```

<210> SEQ ID NO 27
<211> LENGTH: 135
<212> TYPE: PRT
<213> ORGANISM: Cenarchaeum symbiosum

<400> SEQUENCE: 27

```
Thr Val Gln Asp Ala Val Glu Ile Pro Pro Ser Leu Leu Val Ser Ala
 1               5              10              15

Thr Tyr Asp Ser Gln Ala Gly Ala Val Val Leu Lys Phe Tyr Glu Pro
                20              25              30

Glu Ser Gln Lys Ile Val His Trp Thr Asp Asn Thr Gly His Lys Pro
                35              40              45

Tyr Cys Tyr Thr Arg Gln Pro Pro Ser Glu Leu Gly Glu Leu Glu Gly
 50              55              60
```

Arg Glu Asp Val Leu Gly Thr Glu Gln Val Met Arg His Asp Leu Ile
 65                  70                  75                  80

Ala Asp Lys Asp Val Pro Val Thr Lys Ile Thr Val Ala Asp Pro Leu
                 85                  90                  95

Ala Ile Gly Gly Thr Asn Ser Glu Lys Ser Ile Arg Asn Ile Met Asp
                100                 105                 110

Thr Trp Glu Ser Asp Ile Lys Tyr Tyr Glu Asn Tyr Leu Tyr Asp Lys
            115                 120                 125

Ser Leu Val Val Gly Arg Tyr
    130                 135

<210> SEQ ID NO 28
<211> LENGTH: 133
<212> TYPE: PRT
<213> ORGANISM: Sulfolobus acidocaldarius

<400> SEQUENCE: 28

Trp Ile Lys Glu Ala Glu Asp Gly Lys Val Tyr Phe Leu Leu Gln Val
 1               5                  10                  15

Asp Tyr Asp Gly Lys Lys Ser Arg Ala Val Cys Lys Leu Tyr Asp Lys
                 20                  25                  30

Glu Gly Lys Lys Ile Tyr Ile Met Gln Asp Glu Ser Gly His Lys Pro
             35                  40                  45

Tyr Phe Leu Thr Asp Ile Asp Pro Asp Lys Val Asn Lys Ile Thr Lys
     50                  55                  60

Val Val Arg Asp Pro Ser Phe Asp His Leu Glu Leu Ile Asn Lys Val
 65                  70                  75                  80

Asp Pro Tyr Thr Gly Lys Lys Ile Arg Leu Thr Lys Ile Val Val Lys
                 85                  90                  95

Asp Pro Leu Ala Val Arg Arg Met Arg Ser Ser Leu Pro Lys Ala Tyr
                100                 105                 110

Glu Ala His Ile Lys Tyr Tyr Asn Asn Tyr Val Tyr Asp Asn Gly Leu
            115                 120                 125

Ile Pro Gly Leu Ile
    130

<210> SEQ ID NO 29
<211> LENGTH: 133
<212> TYPE: PRT
<213> ORGANISM: Sulfurisphaera ohwakuensis

<400> SEQUENCE: 29

Trp Ile Lys Glu Ala Glu Gly Lys Ser Tyr Phe Leu Leu Gln Val
 1               5                  10                  15

Asp Tyr Asp Gly Lys Lys Ser Lys Ala Ile Cys Lys Leu Tyr Asp Lys
                 20                  25                  30

Glu Thr Lys Lys Ile Tyr Ile Leu Tyr Asp Asn Thr Gly His Lys Pro
             35                  40                  45

Tyr Phe Leu Thr Asp Ile Asp Pro Glu Lys Val Asn Lys Ile Pro Lys
     50                  55                  60

Val Val Arg Asp Pro Ser Phe Asp His Leu Glu Thr Val Ile Lys Ile
 65                  70                  75                  80

Asp Pro Tyr Ser Gly Asn Lys Ile Lys Leu Thr Lys Ile Val Val Lys
                 85                  90                  95

Asp Pro Leu Ala Val Arg Arg Met Arg Asn Ser Val Pro Lys Ala Tyr
                100                 105                 110

```
Glu Ala His Ile Lys Tyr Phe Asn Asn Tyr Ile Tyr Asp Leu Gly Leu
        115                 120                 125

Ile Pro Gly Leu Pro
    130

<210> SEQ ID NO 30
<211> LENGTH: 132
<212> TYPE: PRT
<213> ORGANISM: Sulfolobus solfataricus

<400> SEQUENCE: 30

Trp Leu Glu Glu Ala Gln Glu Asn Lys Ile Tyr Phe Leu Leu Gln Val
1               5                   10                  15

Asp Tyr Asp Gly Lys Lys Gly Lys Ala Val Cys Lys Leu Phe Asp Lys
            20                  25                  30

Glu Thr Gln Lys Ile Tyr Ala Leu Tyr Asp Asn Thr Gly His Lys Pro
        35                  40                  45

Tyr Phe Leu Val Asp Leu Glu Pro Asp Lys Val Gly Lys Ile Pro Lys
    50                  55                  60

Ile Arg Asp Pro Ser Phe Asp His Ile Glu Thr Val Ser Lys Ile Asp
65                  70                  75                  80

Pro Tyr Thr Trp Asn Lys Phe Lys Leu Thr Lys Ile Val Arg Asp
                85                  90                  95

Pro Leu Ala Val Arg Arg Leu Arg Asn Asp Val Pro Lys Ala Tyr Glu
            100                 105                 110

Ala His Ile Lys Tyr Phe Asn Asn Tyr Met Tyr Asp Ile Gly Leu Ile
        115                 120                 125

Pro Gly Met Pro
    130

<210> SEQ ID NO 31
<211> LENGTH: 133
<212> TYPE: PRT
<213> ORGANISM: Pyrodictium occultum

<400> SEQUENCE: 31

Lys Pro Leu Glu Ala Arg Asp Gly Val Glu Gly Phe Leu Leu Gln Thr
1               5                   10                  15

Met Tyr Asp Gly Glu Arg Gly Val Ala Ala Lys Ile Tyr Asp Asp
            20                  25                  30

Arg Asn Gly Ile Val Tyr Val Tyr Phe Asp Arg Thr Gly Tyr Met Pro
        35                  40                  45

Tyr Phe Leu Thr Asp Ile Pro Pro Asp Lys Leu Gln Glu Leu His Glu
    50                  55                  60

Val Val Arg His Lys Gly Phe Asp His Val Glu Val Glu Lys Phe
65                  70                  75                  80

Asp Leu Leu Arg Trp Gln Arg Arg Lys Val Thr Lys Ile Val Val Lys
                85                  90                  95

Thr Pro Asp Val Val Arg Val Leu Arg Asp Lys Val Pro Arg Ala Trp
            100                 105                 110

Glu Ala Asn Ile Lys Phe His His Asn Tyr Ile Tyr Asp Tyr Gly Leu
        115                 120                 125

Val Pro Gly Met Lys
    130

<210> SEQ ID NO 32
<211> LENGTH: 138
<212> TYPE: PRT
```

<213> ORGANISM: Aeropyrum pernix

<400> SEQUENCE: 32

```
Val Arg Glu Pro Trp Val Glu Ser Val Arg Gly Tyr Leu Leu Asp Val
1               5                   10                  15

Arg Tyr Asp Gly Ser Leu Gly Lys Ala Val Leu Met Leu Tyr Asp Pro
            20                  25                  30

Ser Ser Gly Ser Leu Val Lys Trp Ala Asp Arg Thr Gly His Lys Pro
            35                  40                  45

Tyr Phe Leu Thr Asp Ala Arg Pro Glu Asp Leu Arg Ala Ala Gly Val
            50                  55                  60

Asp Val Ser His Asp Glu Ser Phe Leu Gln Tyr Asp Leu Val Glu Lys
65                  70                  75                  80

Phe His Pro Ile Asp Arg Lys Leu Val Lys Leu Tyr Lys Ile Val Val
                85                  90                  95

Ser Asp Pro Leu Ala Val Arg Arg Leu Arg Glu Lys Val Ser Ser Ala
            100                 105                 110

Gly Phe Ser Val Trp Glu Ala Asp Ile Lys Tyr His His Asn Tyr Ile
            115                 120                 125

Phe Asp Arg Gln Leu Ile Pro Gly Ile Leu
            130                 135
```

<210> SEQ ID NO 33
<211> LENGTH: 14
<212> TYPE: PRT
<213> ORGANISM: Unknown
<220> FEATURE:
<223> OTHER INFORMATION: amino acid motif where X can be any amino acid

<400> SEQUENCE: 33

```
Glu Xaa Xaa Ile Xaa Phe Tyr Xaa Xaa Xaa Tyr Xaa Xaa Asp
1               5                   10
```